(12) United States Patent
Bayer et al.

(10) Patent No.: US 11,229,765 B2
(45) Date of Patent: Jan. 25, 2022

(54) HUMIDIFIER RESERVOIR

(71) Applicant: RESMED PTY LTD, Bella Vista (AU)

(72) Inventors: Christian Bayer, Penzberg (DE); Bernd Christoph Lang, Graefelfing (DE); Mark Bertinetti, Sydney (AU); Johann Sebastian Burz, Germaringen (DE); Robert Eibl, Bad Toelz (DE); Martin Kasparbauer, Munich (DE); Andreas Kirchberger, Miesbach (DE); Johannes Nickol, Neukenroth (DE); Jens Rothfuss, Unterschleissheim (DE)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 16/346,329

(22) PCT Filed: Nov. 21, 2017

(86) PCT No.: PCT/AU2017/051276
§ 371 (c)(1),
(2) Date: Apr. 30, 2019

(87) PCT Pub. No.: WO2018/094452
PCT Pub. Date: May 31, 2018

(65) Prior Publication Data
US 2019/0298964 A1  Oct. 3, 2019

(30) Foreign Application Priority Data

Nov. 22, 2016 (AU) ................................ 2016904769

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0816* (2013.01); *A61M 16/109* (2014.02);
(Continued)

(58) Field of Classification Search
CPC .... A61M 16/10; A61M 16/1075–1095; A61M 16/14; A61M 16/16–168;
(Continued)

(56) References Cited

U.S. PATENT DOCUMENTS

| 4,012,473 A | 3/1977 | Lindsey et al. |
| 4,201,737 A * | 5/1980 | Carden ..................... H05B 3/68 |
| | | 261/142 |

(Continued)

FOREIGN PATENT DOCUMENTS

| AU | 2016203593 B1 | 11/2016 |
| CN | 103747828 A | 4/2014 |

(Continued)

OTHER PUBLICATIONS

"Respiratory Physiology", by John B. West, Lippincott Williams & Wilkins, 9th edition published 2012, 8 pages.
(Continued)

*Primary Examiner* — Rachel T Sippel
(74) *Attorney, Agent, or Firm* — Nixon & Vanderhye P.C.

(57) ABSTRACT

A water reservoir for an apparatus for humidifying a flow of breathable gas includes a reservoir base including a cavity structured to hold a volume of liquid and a conductive portion provided to the base. The conductive portion is adapted to thermally engage with a heater plate to allow thermal transfer of heat from the heater plate to the volume of liquid. The conductive portion includes a thin film comprising a non-metallic material, and the thin film includes a wall thickness less than about 1 mm.

27 Claims, 22 Drawing Sheets

(51) Int. Cl.
*A61M 16/08* (2006.01)
*A61M 16/00* (2006.01)
*A61M 11/04* (2006.01)
*A61M 16/06* (2006.01)

(52) U.S. Cl.
CPC ........... *A61M 11/042* (2014.02); *A61M 16/06* (2013.01); *A61M 16/108* (2014.02); *A61M 16/161* (2014.02); *A61M 2016/0027* (2013.01); *A61M 2016/0033* (2013.01); *A61M 2016/0039* (2013.01); *A61M 2205/3303* (2013.01); *A61M 2205/3368* (2013.01); *A61M 2205/50* (2013.01); *A61M 2209/086* (2013.01)

(58) Field of Classification Search
CPC .. A61M 2209/086; F24F 1/0083; F24F 1/037; F24F 3/14; F24F 6/00; F24F 6/02–025; F24F 2006/006–008; F24F 11/0008
See application file for complete search history.

(56) References Cited

U.S. PATENT DOCUMENTS

| | | | |
|---|---|---|---|
| 4,782,832 A | 11/1988 | Trimble et al. | |
| 4,944,310 A | 7/1990 | Sullivan | |
| 5,687,115 A | 11/1997 | Landis | |
| 6,532,959 B1 | 3/2003 | Berthon-Jones | |
| 6,581,594 B1 | 6/2003 | Drew et al. | |
| 7,096,864 B1* | 8/2006 | Mayer | A61M 16/0066 128/202.27 |
| 7,413,173 B2 | 8/2008 | DiMatteo et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,820,322 B1 | 9/2014 | Gordon | |
| 2003/0066526 A1* | 4/2003 | Thudor | A61M 16/161 128/203.26 |
| 2009/0000620 A1 | 1/2009 | Virr | |
| 2009/0044808 A1 | 2/2009 | Guney et al. | |
| 2009/0050156 A1 | 2/2009 | Ng et al. | |
| 2010/0000534 A1 | 1/2010 | Kooh et al. | |
| 2010/0147299 A1* | 6/2010 | Row | H05B 3/46 128/203.27 |
| 2013/0081582 A1 | 4/2013 | Varga | |
| 2013/0081618 A1 | 4/2013 | Korneff et al. | |
| 2013/0081621 A1 | 4/2013 | Korneff et al. | |
| 2014/0001658 A1 | 1/2014 | Virr | |
| 2014/0352694 A1 | 12/2014 | Row et al. | |
| 2015/0030317 A1* | 1/2015 | Bayer | A61M 16/16 392/403 |
| 2015/0115483 A1 | 4/2015 | Miller | |

FOREIGN PATENT DOCUMENTS

| | | | |
|---|---|---|---|
| CN | 105636632 A | 6/2016 | |
| WO | 98/004310 A1 | 2/1998 | |
| WO | 98/034665 A1 | 8/1998 | |
| WO | 2000/078381 A1 | 12/2000 | |
| WO | 2004/073778 A1 | 9/2004 | |
| WO | 2005/063328 A1 | 7/2005 | |
| WO | 2006/074513 A1 | 7/2006 | |
| WO | 2006/130903 A1 | 12/2006 | |
| WO | 2009/052560 A1 | 4/2009 | |
| WO | 2010/135785 A1 | 12/2010 | |
| WO | 2012/171072 A1 | 12/2012 | |
| WO | 2013/020167 A1 | 2/2013 | |
| WO | 2013/049660 A2 | 4/2013 | |
| WO | 2013/135318 A1 | 9/2013 | |
| WO | 2014/138804 A1 | 9/2014 | |
| WO | WO-2015013761 A1 * | 2/2015 | ......... A61M 16/026 |
| WO | WO 2015/058255 A1 | 4/2015 | |
| WO | 2017/109737 A1 | 6/2017 | |

OTHER PUBLICATIONS

International Search Report and Written Opinion of the ISA dated Feb. 1, 2018 in International Application No. PCT/AU2017/051276, 7 pages.
Written Opinion of the International Searching Authority dated Feb. 1, 2018 in International Application No. PCT/AU2017/051276, 7 pages.
International Preliminary Report on Patentability dated Nov. 1, 2018 in International Application No. PCT/AU2017/051276, 13 pages.
First Office Action dated Mar. 5, 2021 in Chinese Application No. 201780072867.X, with English translation, 15 pages.
Notice of Reasons for Rejection dated Oct. 4, 2021 in Japanese Application No. 2019-527347, with English translation, 11 pages.

* cited by examiner

Copyright 2012 ResMed Limited

Relatively Large Positive Curvature

Relatively Small Positive Curvature

Zero Curvature

Relatively Small Negative Curvature

Relatively Large Negative Curvature

Copyright 2015 ResMed Limited

Copyright 2015 ResMed Limited

Left-hand rule

Right-hand rule

Left ear helix

Right-hand helix
Right-hand positive

Right ear helix

HUMIDIFIER RESERVOIR

1 CROSS-REFERENCE TO RELATED APPLICATIONS

This application is the U.S. national phase of International Application No. PCT/AU2017/051276 filed Nov. 21, 2017 which designated the U.S. and claims the benefit of Australian Provisional Application No. 2016904769, filed Nov. 22, 2016, the entire contents of each of which are hereby incorporated by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |

-continued

| Mask name | Mask type | A-weighted sound power level dB(A) (uncertainty) | A-weighted sound pressure dB(A) (uncertainty) | Year (approx.) |
|---|---|---|---|---|
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology relates to a humidifier including a water reservoir comprising a non-metallic, thin film base adapted to thermally engage with a heater plate. The thin film base of the water reservoir is structured to provide an arrangement that reduces cost of production of the water reservoir, while retaining, or improving, its heat transfer characteristics as well as its reliability. In an example, the thin film base may be sufficiently thin and flat to provide good thermal contact and good humidifier performance and allow a suitable material to be selected, e.g., depending on humidifier requirements and performance.

An aspect of the present technology relates to a water reservoir for an apparatus for humidifying a flow of breathable gas including a reservoir base including a cavity structured to hold a volume of liquid and a conductive portion provided to the base. The conductive portion is adapted to thermally engage with a heater plate to allow thermal transfer of heat from the heater plate to the volume of liquid. The conductive portion includes a thin film comprising a non-metallic material, and the thin film includes a wall thickness less than about 1 mm.

In an example, the wall thickness of the thin film may be less than about 0.5 mm. In an example, the thin film may comprise silicone, polycarbonate, or other thermoplastic or elastomeric materials. In an example, the thin film may be provided as a separate and distinct structure from the reservoir base. In an example, the thin film comprises a pre-formed structure that is secured or otherwise provided to the reservoir base. In an example, the reservoir base may include a hole structured to receive the thin film. In an example, the thin film may include a shape that corresponds to a shape of the hole. In an example, the thin film may be generally planar. In an example, the thin film may include a first side adapted to form a bottom interior surface of the water reservoir exposed to the volume of liquid and a second side, opposite to the first side, adapted to form a bottom exterior surface of the water reservoir exposed to the heater plate. In an example, the second side of the thin film may provide a contact surface structured and arranged to directly engage with the heater plate. In an example, the non-metallic material of the thin film may be similar to a material of the reservoir base. In an example, the wall thickness of the thin film may be less than a wall thickness of walls of the reservoir base. In an example, the water reservoir may further comprise one or more ribs structured and arranged to extend across the thin film so as to create a force adapted to push the thin film against the heater plate. In an example, the reservoir base may include a base upper body, a base bottom plate, and the thin film which together form the cavity. In an example, the water reservoir may further comprise a reservoir lid movably connected to the reservoir base to allow the water reservoir to be convertible between an open configuration and a closed configuration.

Another aspect of the present technology relates to a water reservoir for an apparatus for humidifying a flow of breathable gas including a reservoir base including a cavity structured to hold a volume of liquid and a conductive portion provided to the base. The conductive portion is adapted to thermally engage with a heater plate to allow thermal transfer of heat from the heater plate to the volume of liquid. The conductive portion includes a thin film comprising a non-metallic material. The thin film is provided as a separate and distinct structure from the reservoir base, and the thin film includes a wall thickness that is less than a wall thickness of walls of the reservoir base. In an example, the thin film may comprise a pre-formed structure that is secured or otherwise provided to the reservoir base.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

4.3 Patient Interface

Figure 3A:
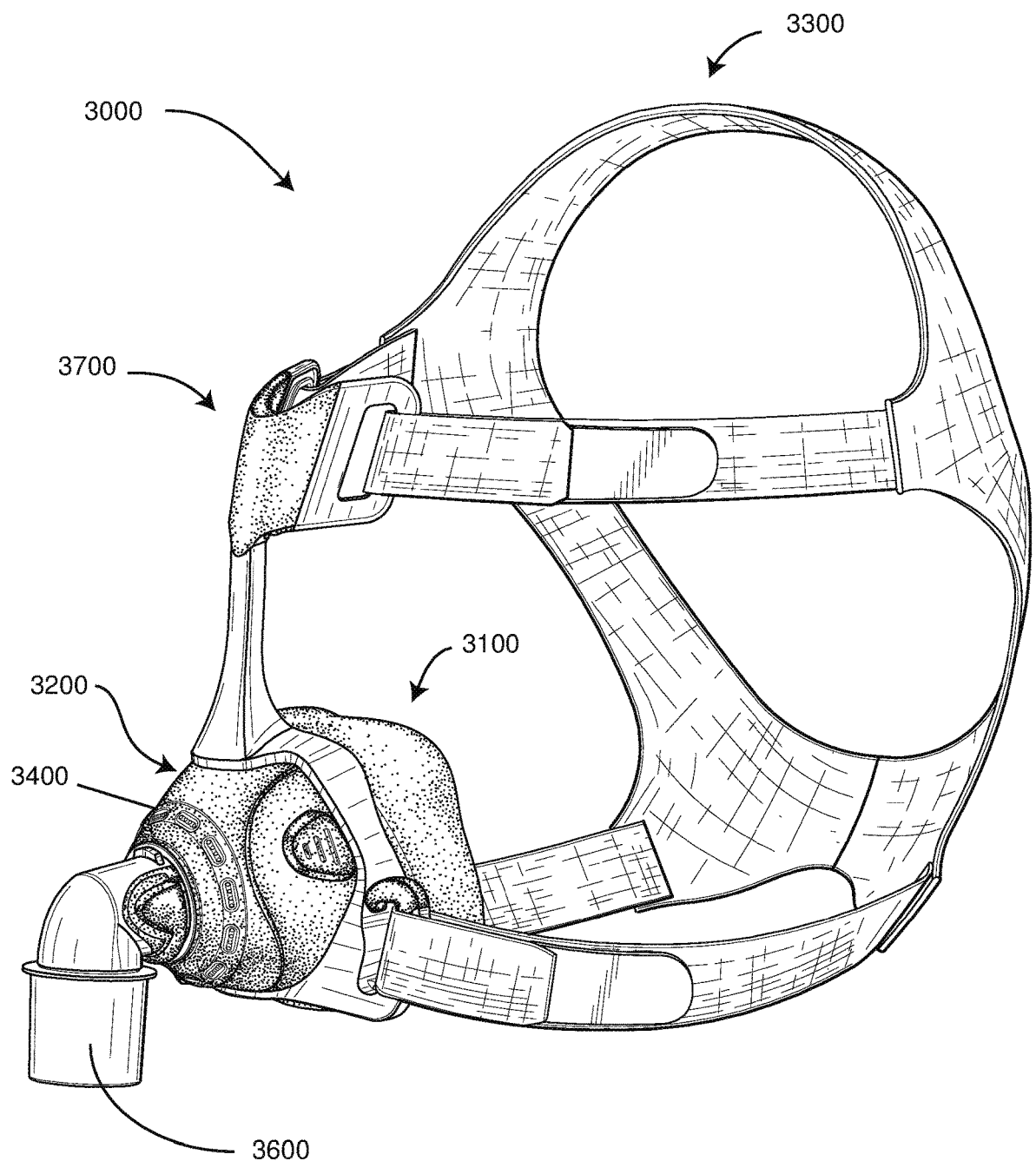

FIG. 3A shows a patient interface in the form of a nasal mask in accordance with one form of the present technology.

Figure 3B:
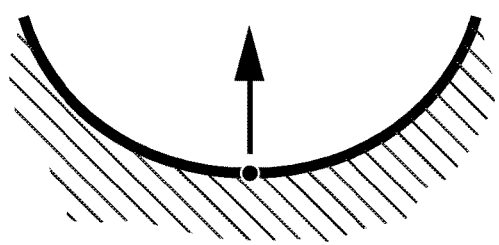

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
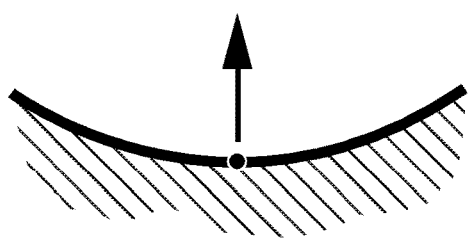

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
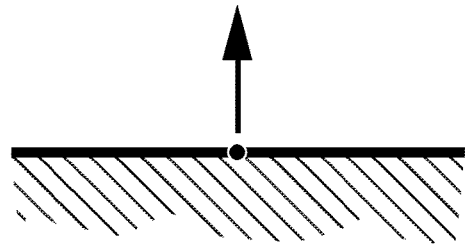

FIG. 3D shows a schematic of a cross-section through a structure at a point. An outward normal at the point is indicated. The curvature at the point has a value of zero.

Figure 3E:
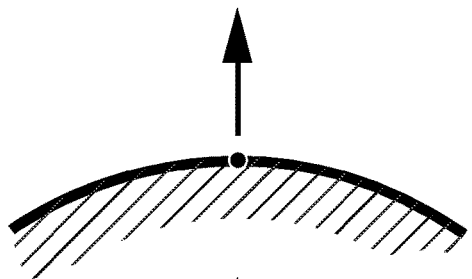

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
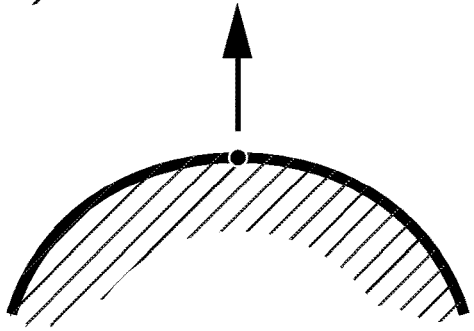

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
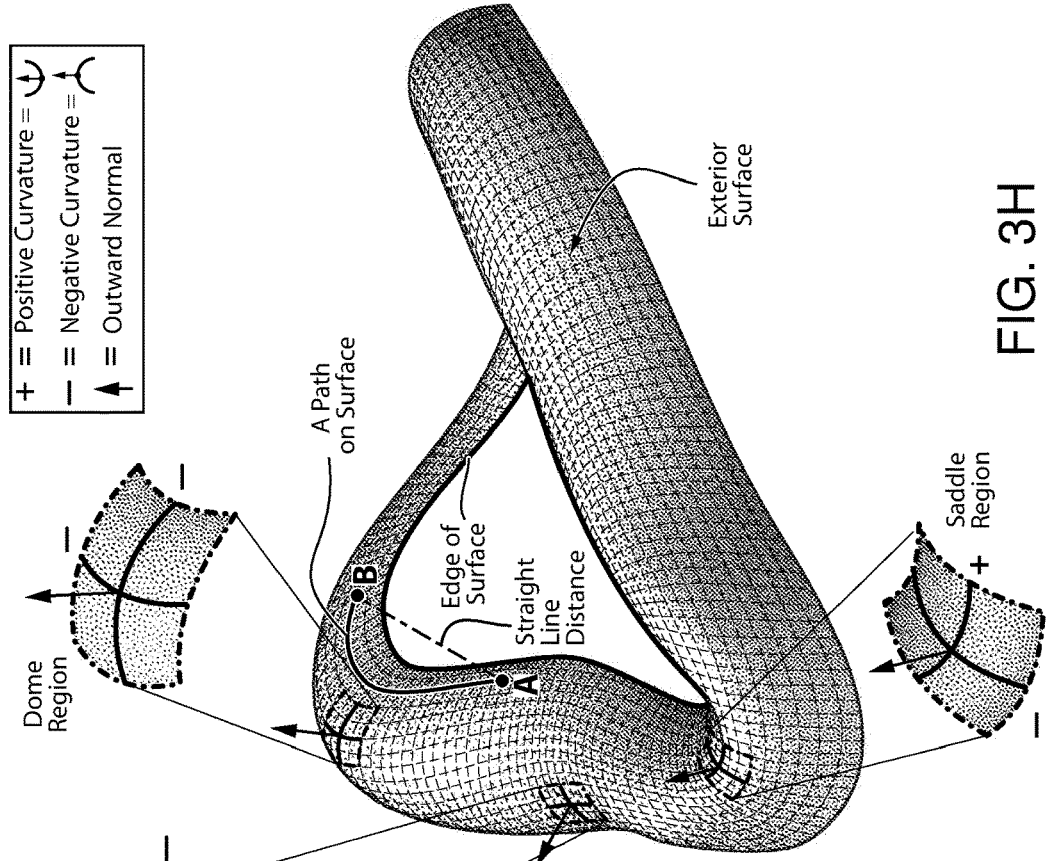
Figure 3G:
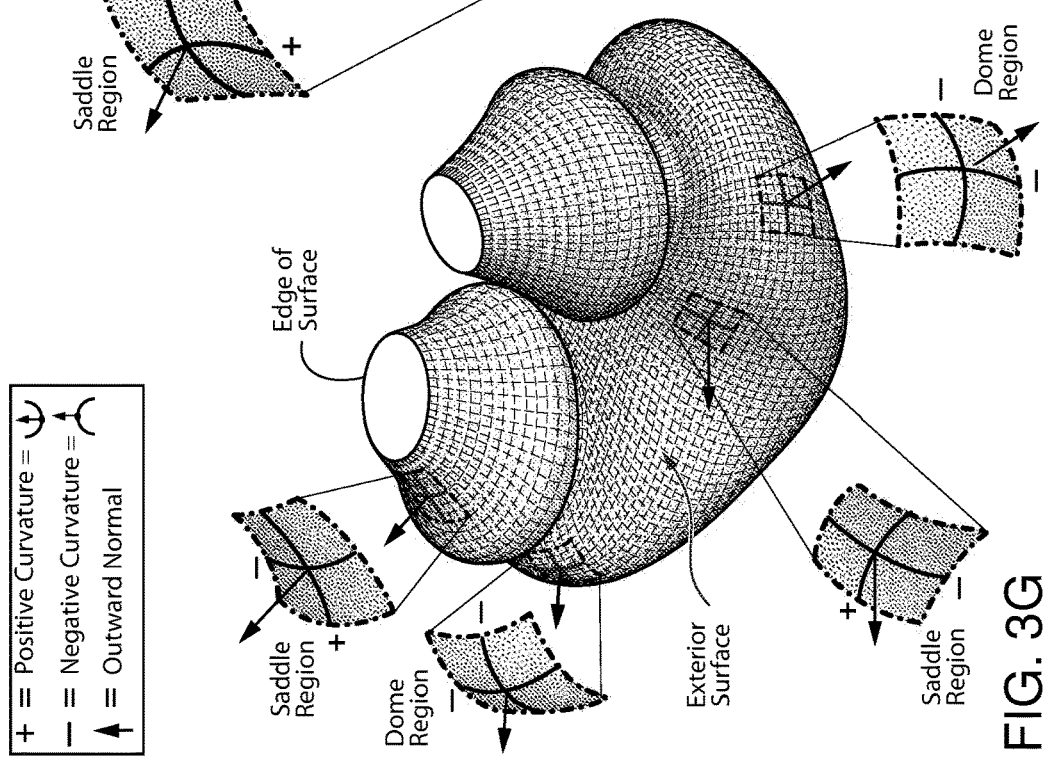

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
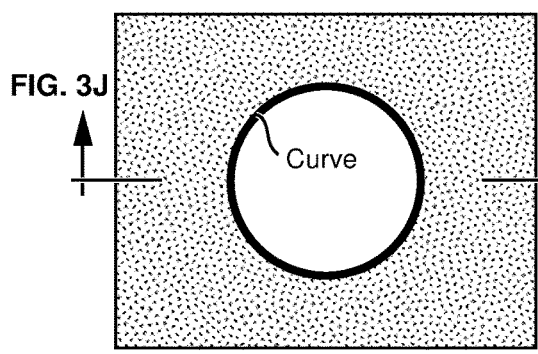

FIG. 3I shows the surface of a structure, with a one dimensional hole in the surface. The illustrated plane curve forms the boundary of a one dimensional hole.

Figure 3K:
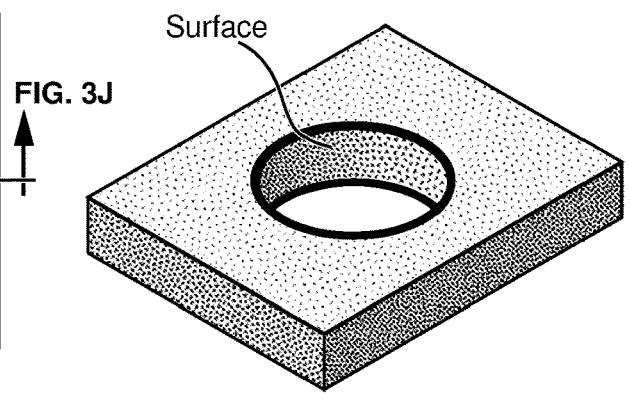
Figure 3J:
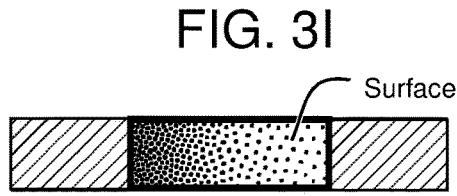

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
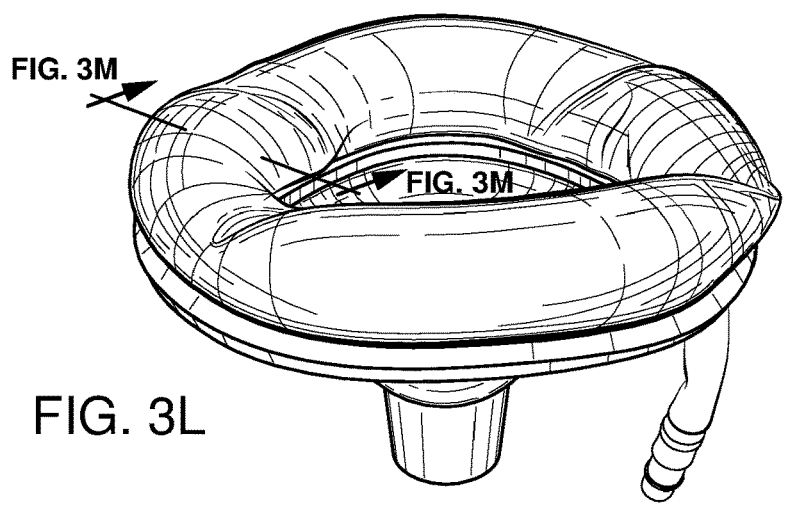

FIG. 3L shows a mask having an inflatable bladder as a cushion.

Figures 3M, 3N:
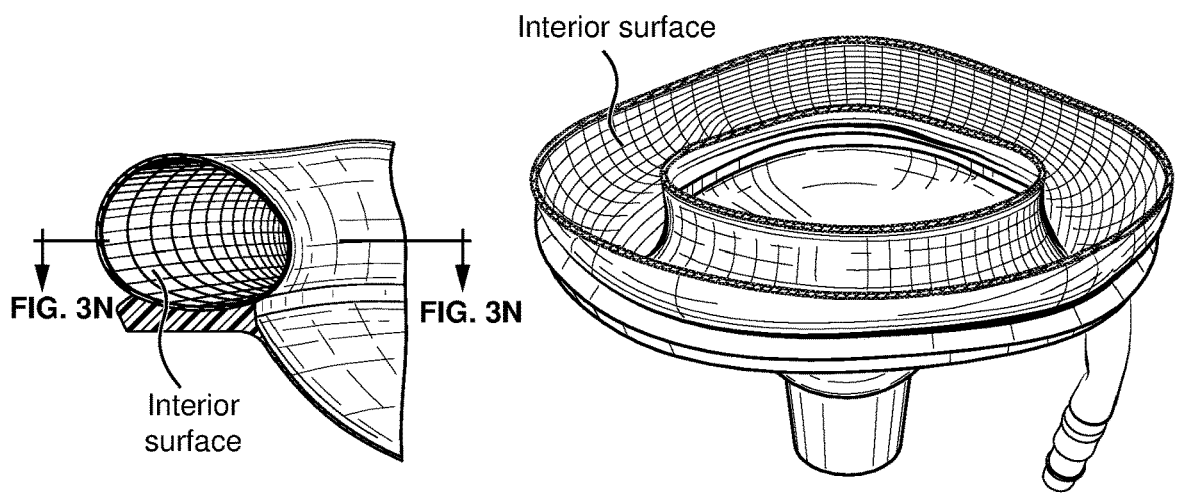

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
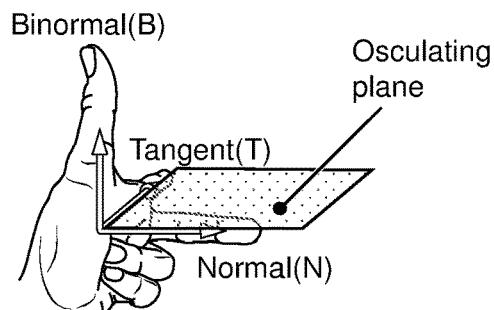

FIG. 3O illustrates a left-hand rule.

Figure 3P:
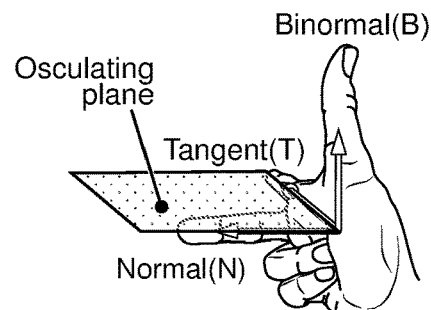

FIG. 3P illustrates a right-hand rule.

Figure 3Q:
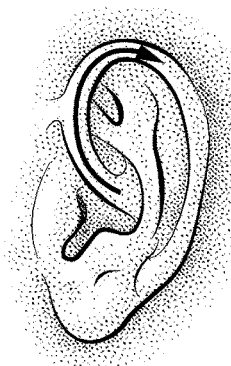

FIG. 3Q shows a left ear, including the left ear helix.

Figure 3S:
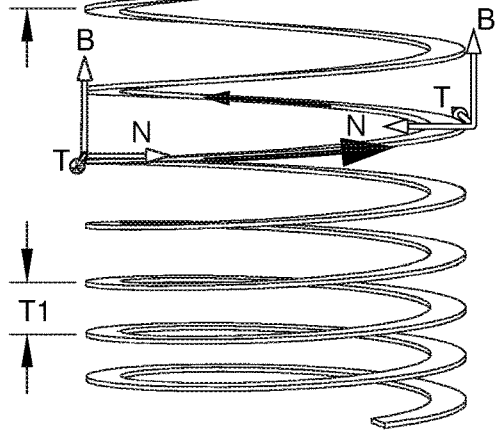
Figure 3R:
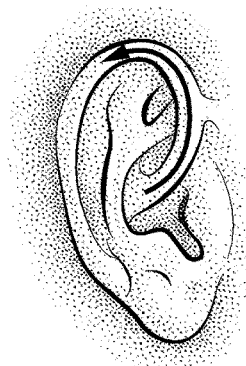

FIG. 3R shows a right ear, including the right ear helix.

FIG. 3S shows a right-hand helix.

Figure 3T:
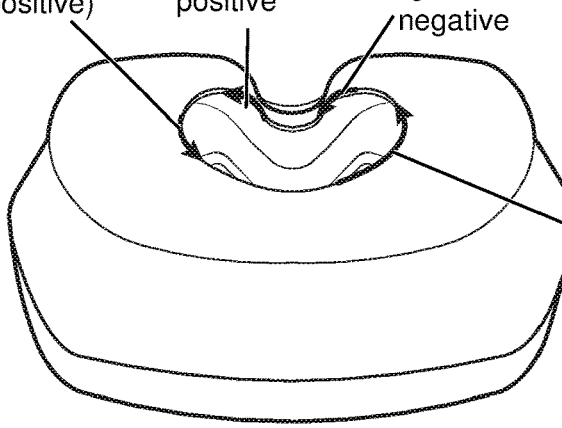

FIG. 3T shows a view of a mask, including the sign of the torsion of the space curve defined by the edge of the sealing membrane in different regions of the mask.

4.4 RPT Device

Figure 4A:
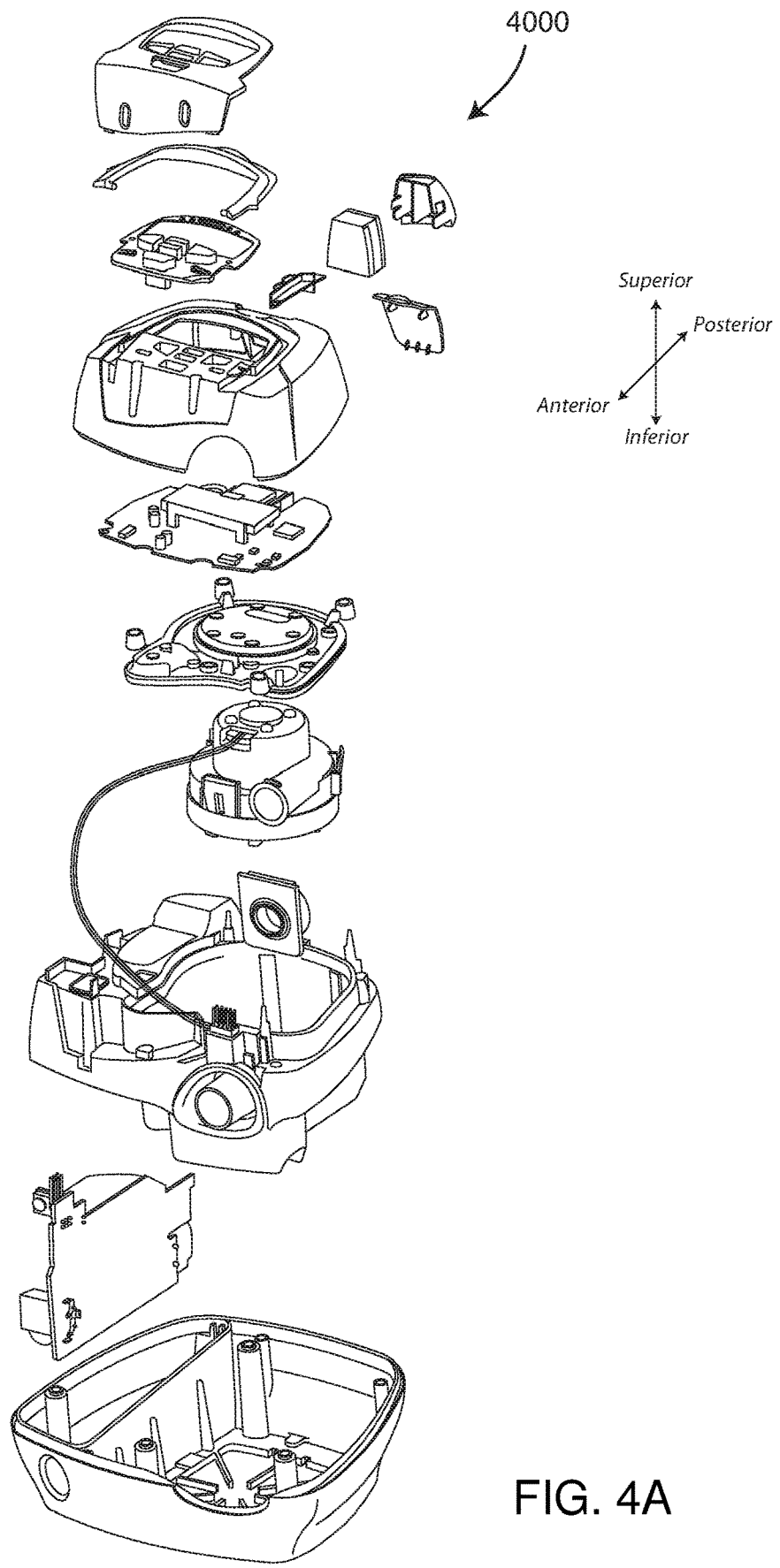

FIG. 4A shows an RPT device in accordance with one form of the present technology.

4.5 Humidifier

Figure 5:
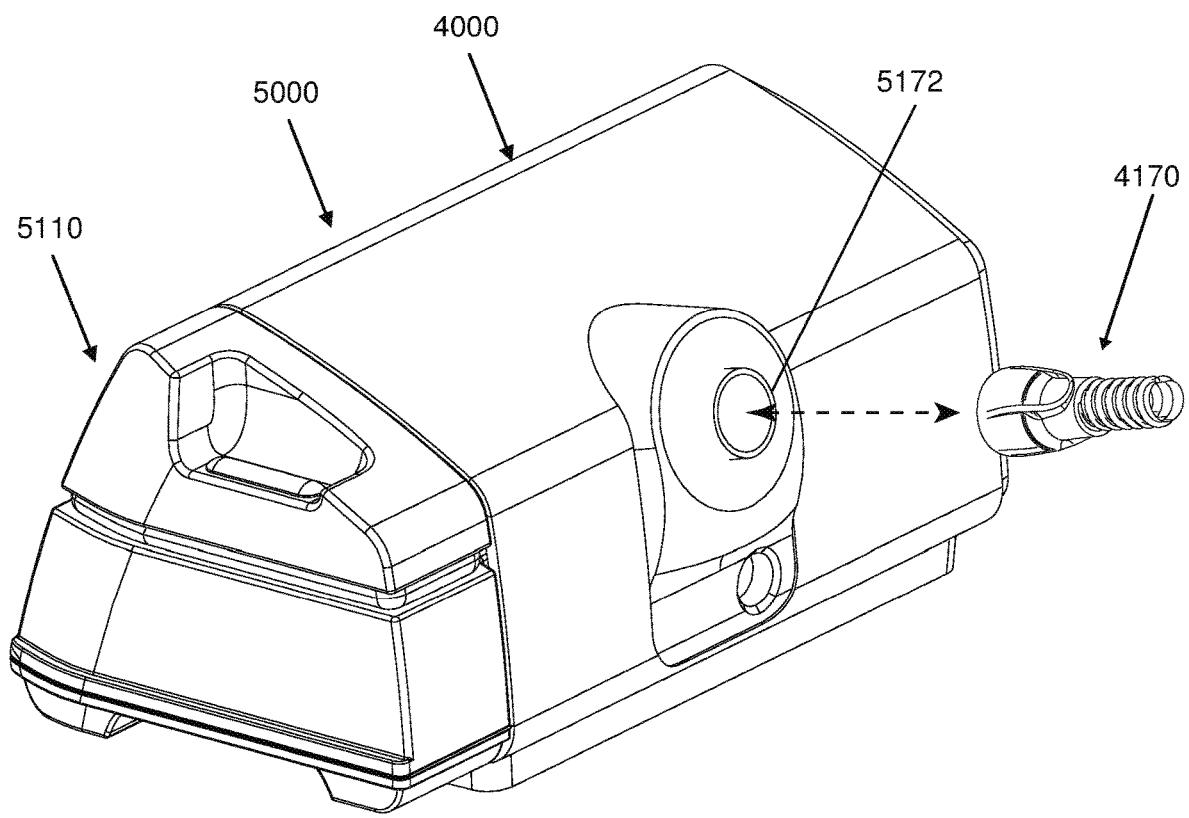

FIG. 5 is a perspective view of an RPT device and an integrated humidifier according to an example of the present technology, and demonstrating engagement of the humidifier with the air circuit according to an example of the present technology.

Figure 6:
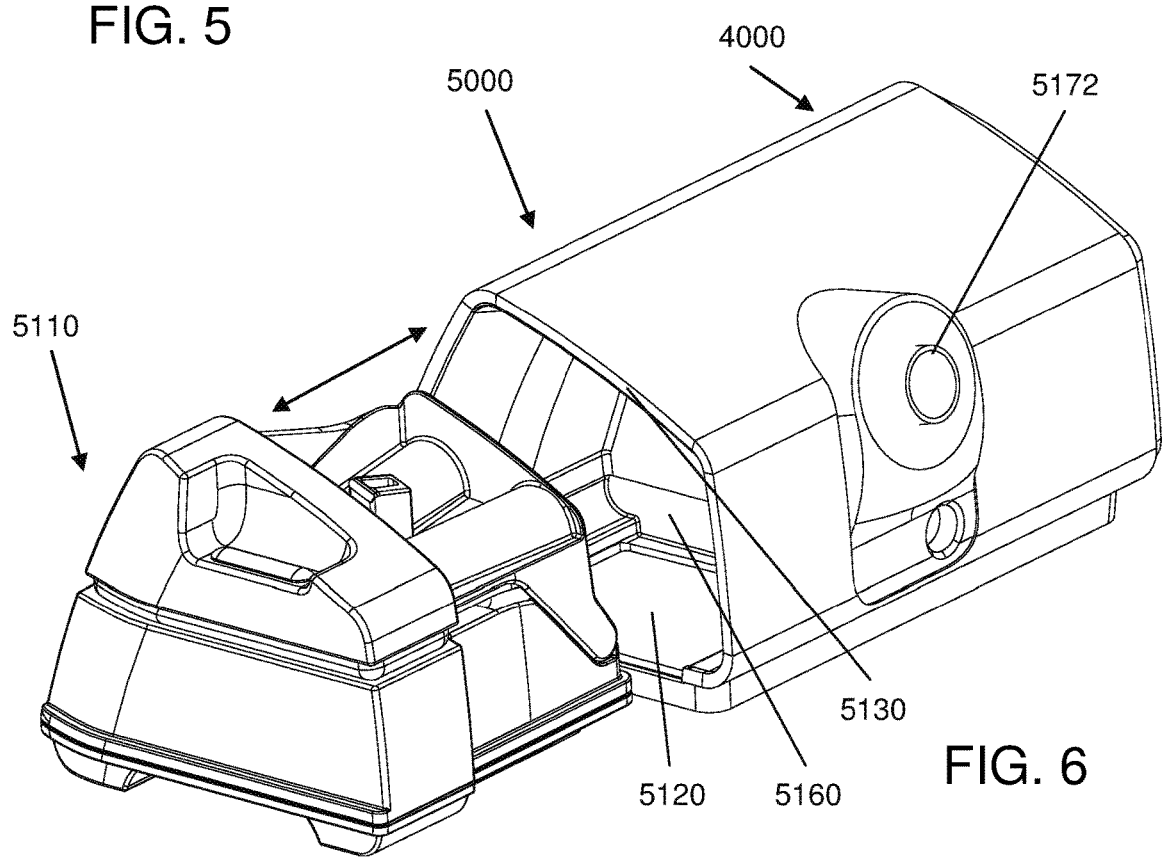

FIG. 6 is a perspective view of the RPT device and integrated humidifier of FIG. 5 demonstrating engagement of the humidifier reservoir with the reservoir dock according to an example of the present technology.

Figure 7:
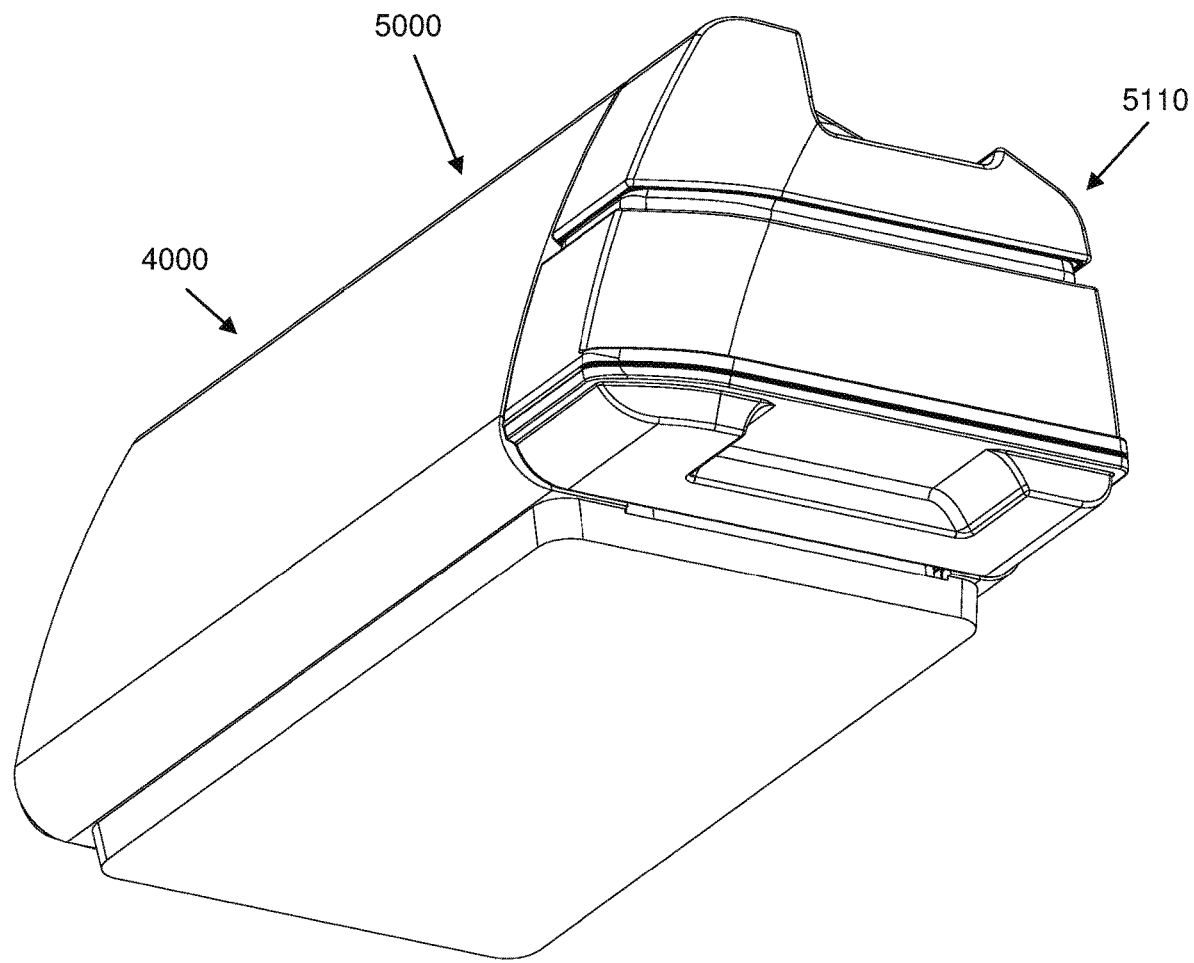

FIG. 7 is another perspective view of the RPT device and integrated humidifier of FIG. 5.

Figure 8:
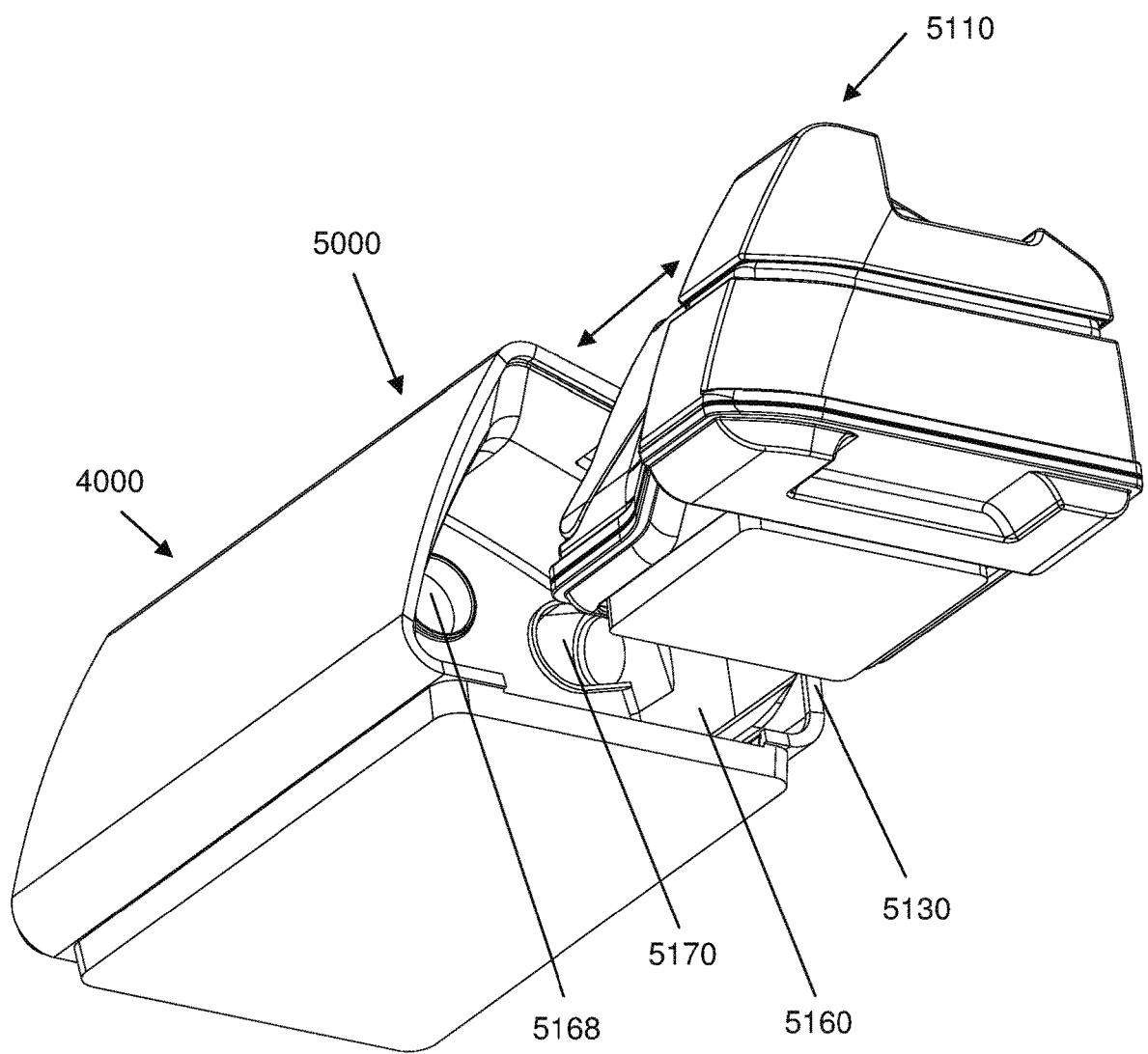

FIG. 8 is another perspective view of the RPT device and integrated humidifier of FIG. 5 demonstrating engagement of the humidifier reservoir with the reservoir dock according to an example of the present technology.

Figure 9:
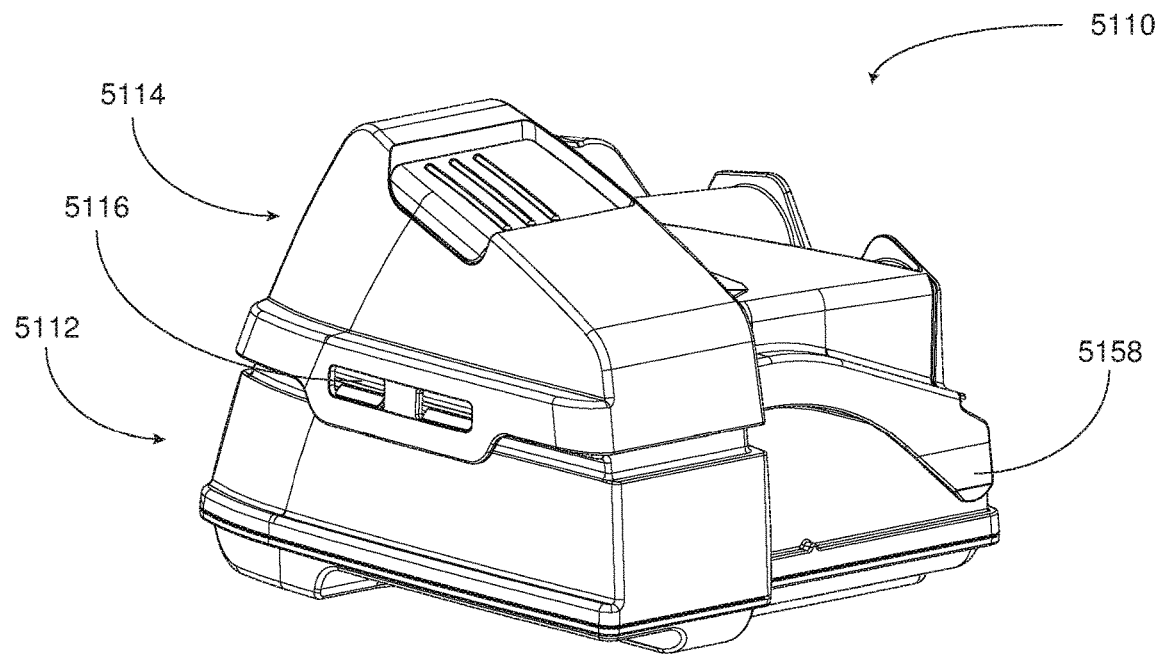
Figure 10:
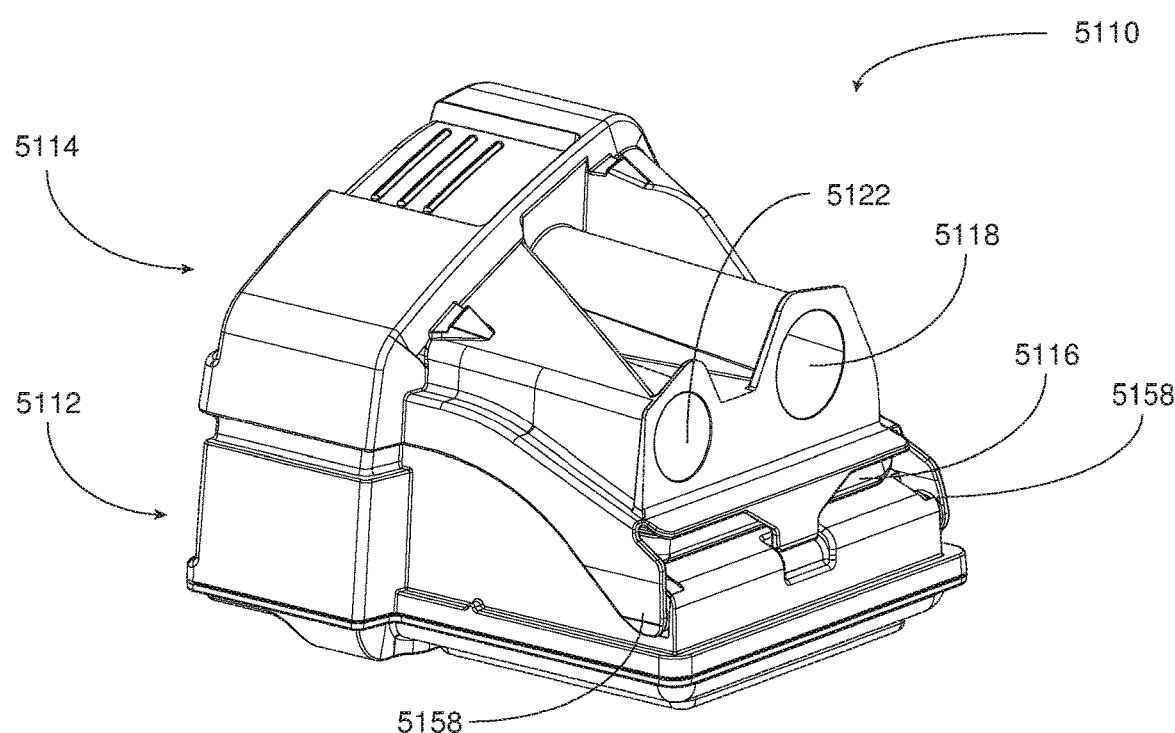
Figure 11:
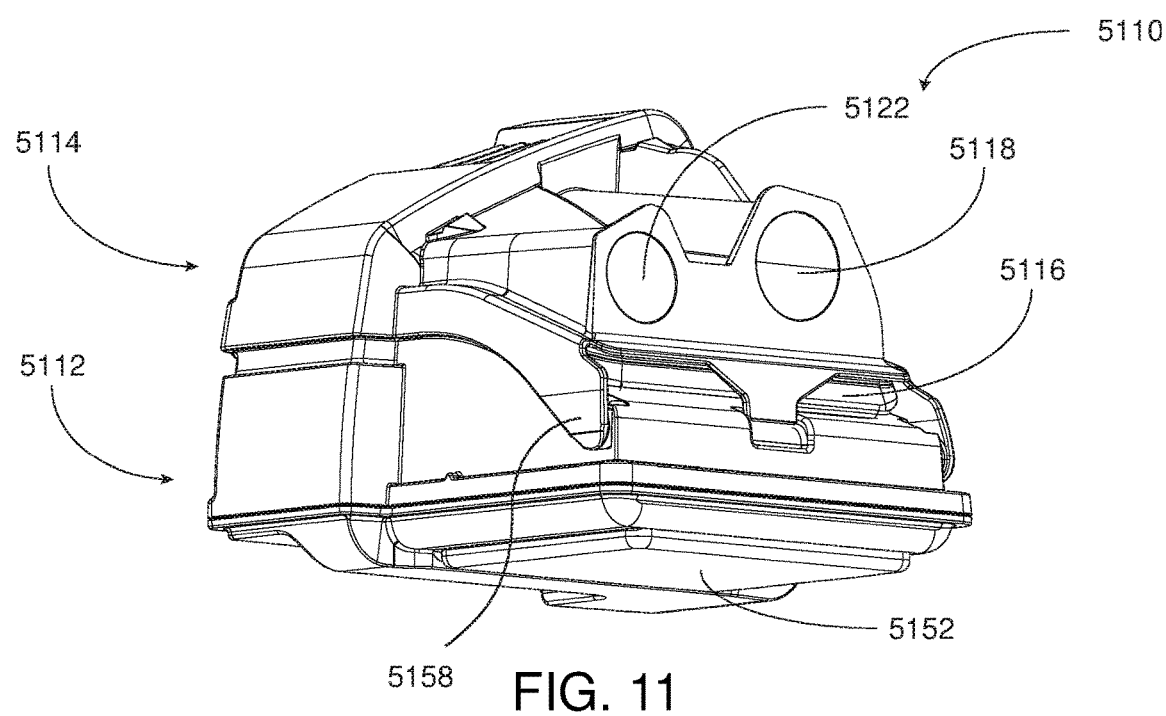
Figure 12:
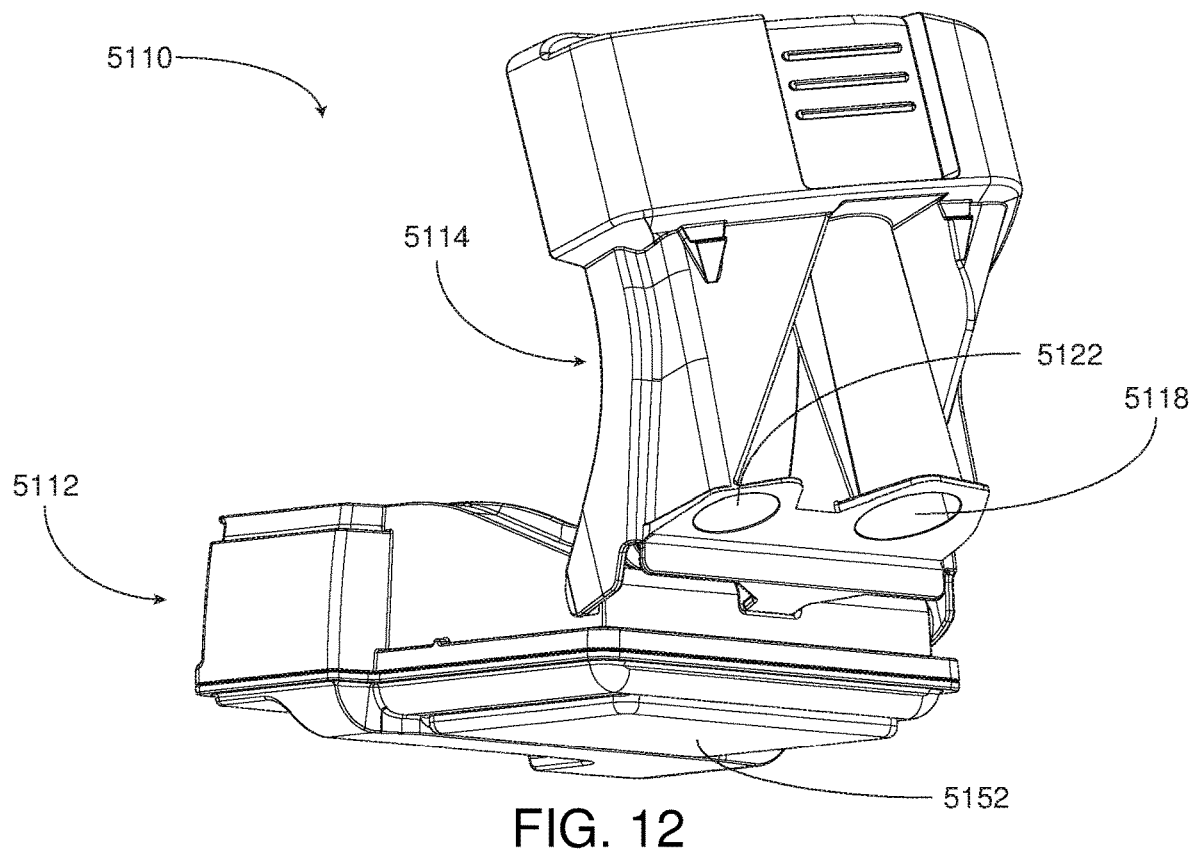

FIGS. 9 to 12 show various views of a humidifier reservoir according to an example of present technology, wherein FIGS. 9 to 11 show the humidifier reservoir in a closed configuration and FIG. 12 shows the humidifier reservoir in an open configuration.

Figure 13:
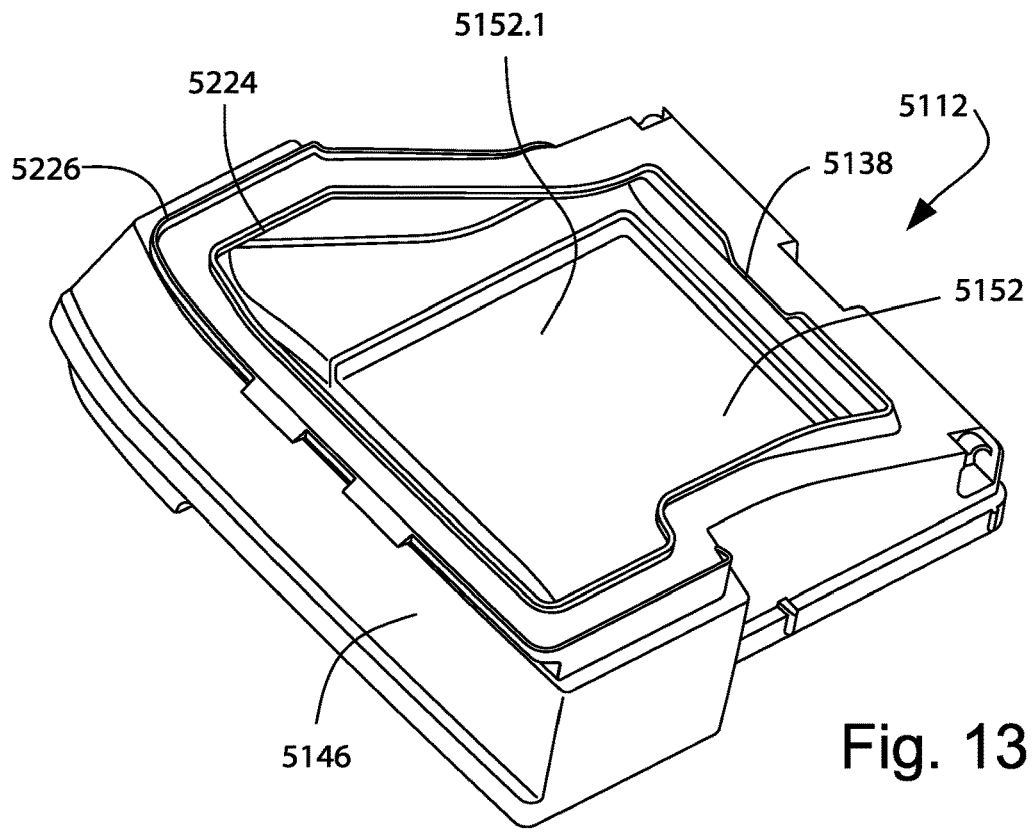

FIG. 13 is a top perspective view of a reservoir base of a humidifier reservoir according to an example of present technology.

Figure 14:
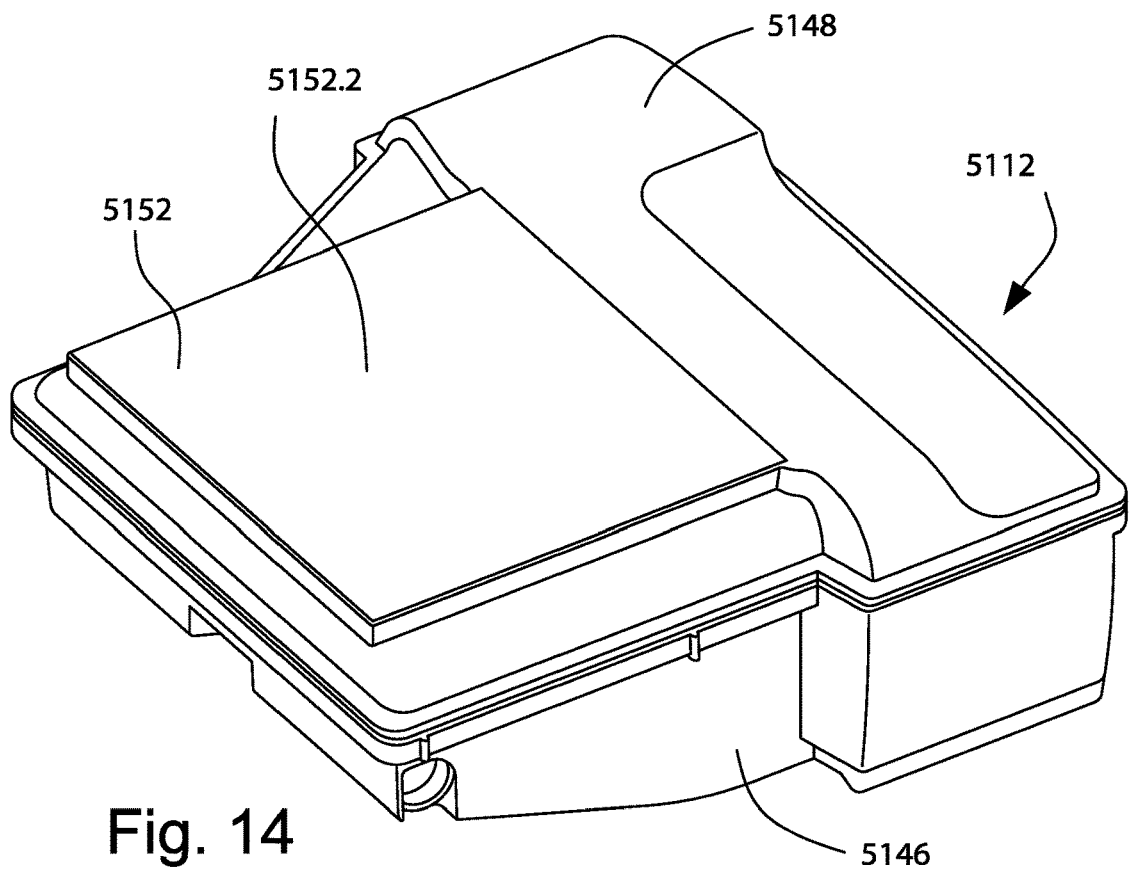

FIG. 14 is a bottom perspective view of the reservoir base of FIG. 13.

Figure 15:
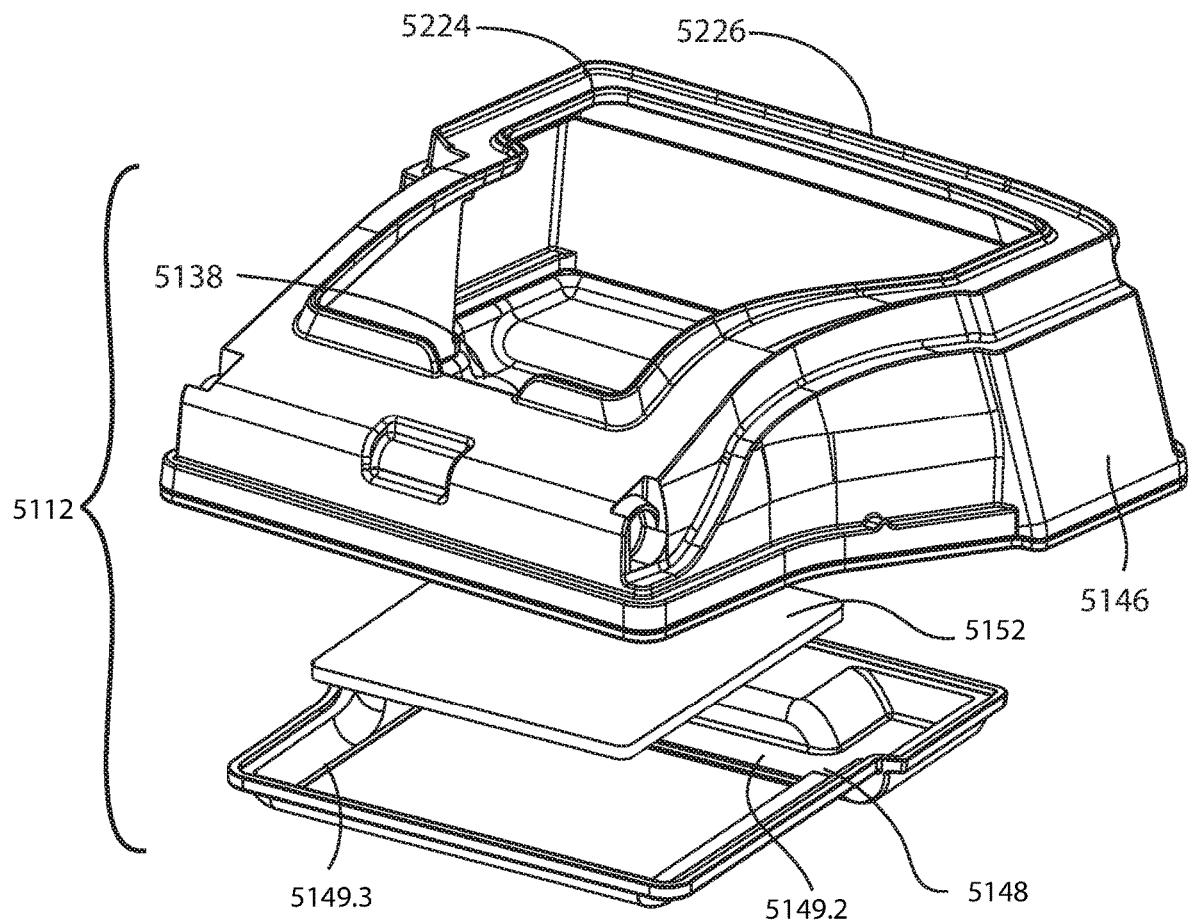

FIG. 15 is an exploded view of the reservoir base of FIG. 13.

Figure 16:
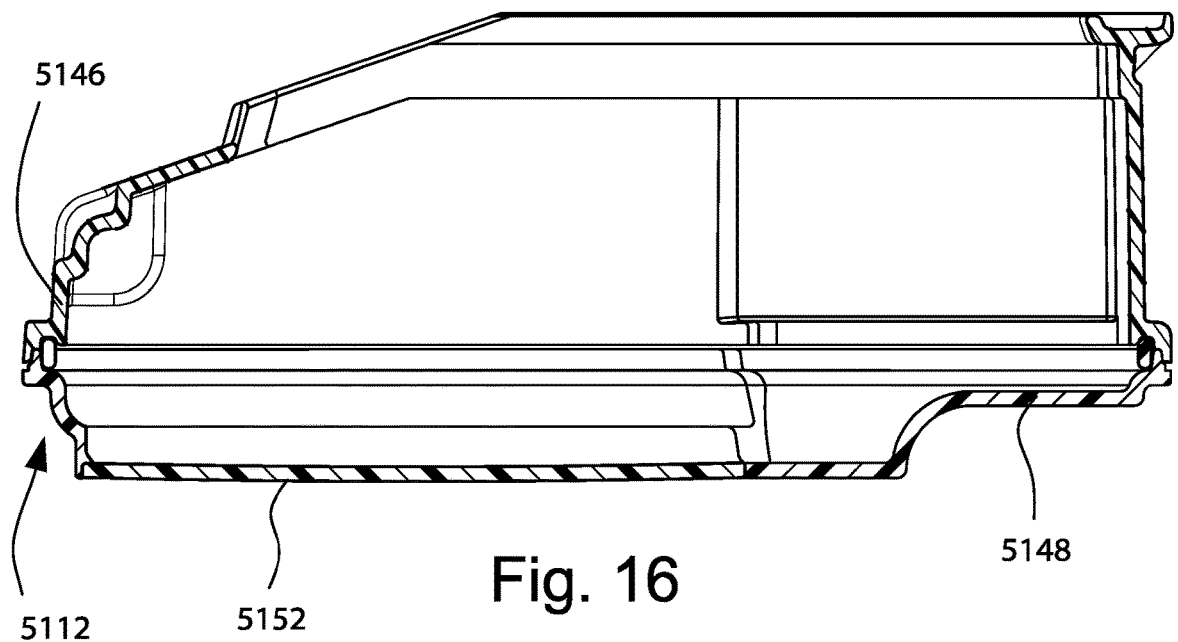

FIG. 16 is a cross-sectional view of a humidifier reservoir including the reservoir base of FIG. 13 according to an example of present technology.

Figure 17:
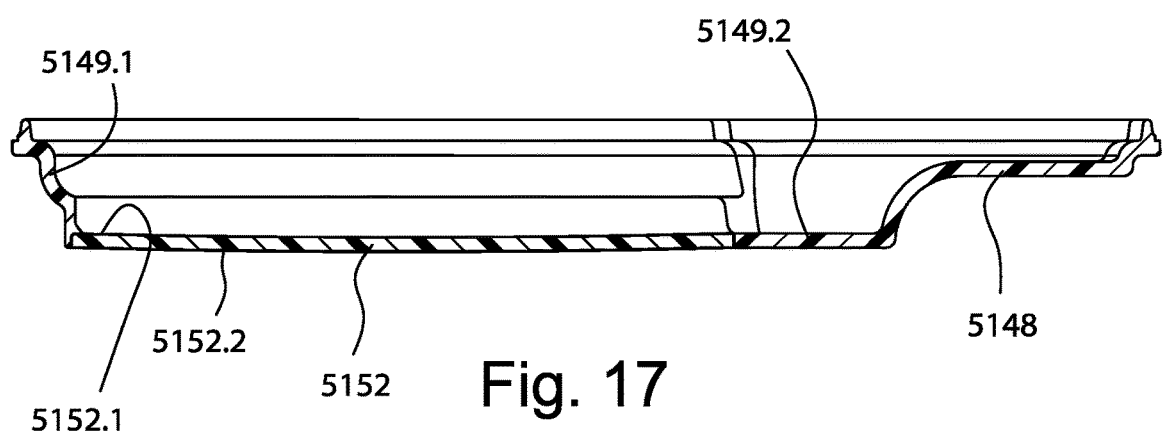

FIG. 17 is a cross-sectional view of a base bottom plate and conductive portion of the reservoir base of FIG. 13 according to an example of present technology.

Figure 18:
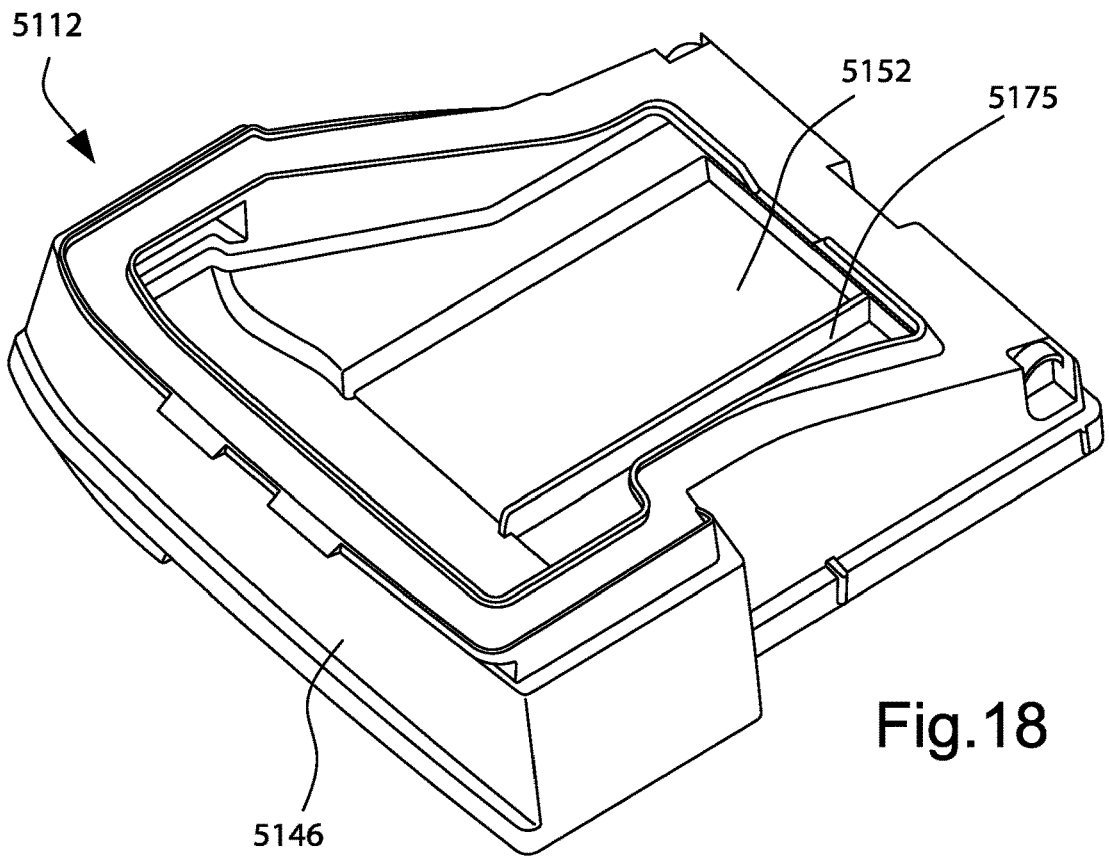

FIG. 18 is a top perspective view of a reservoir base of a humidifier reservoir according to another example of present technology.

Figure 19:
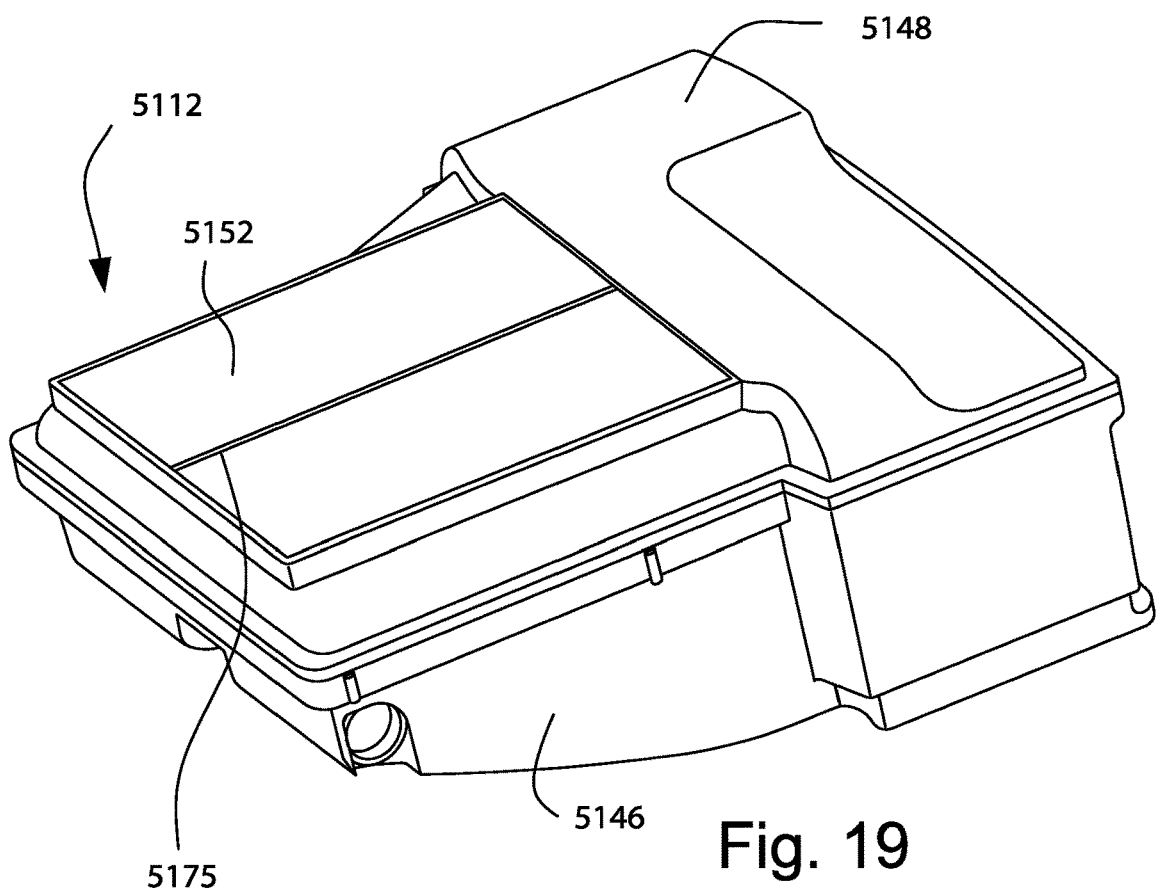

FIG. 19 is a bottom perspective view of the reservoir base of FIG. 18.

Figure 20:
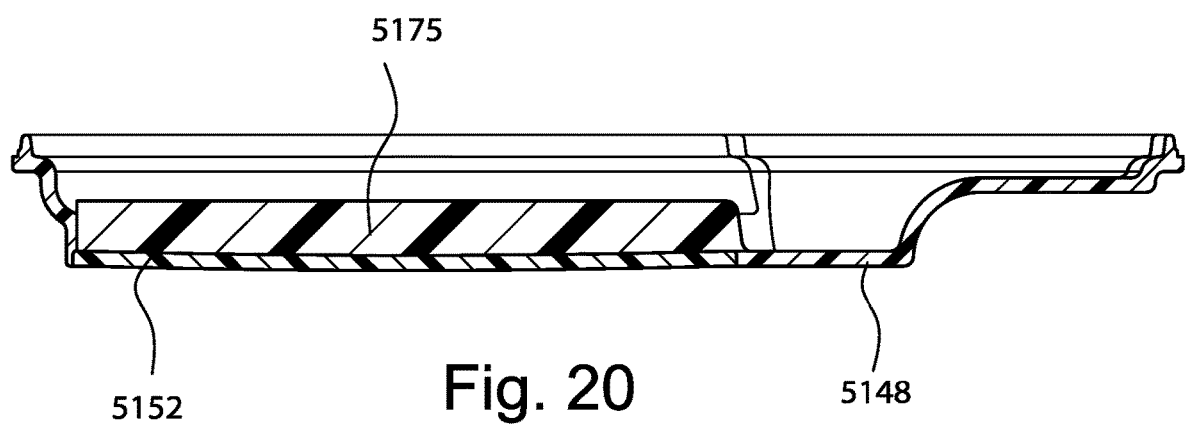

FIG. 20 is a cross-sectional view of a base bottom plate and conductive portion of the reservoir base of FIG. 18 according to an example of present technology.

Figure 21:
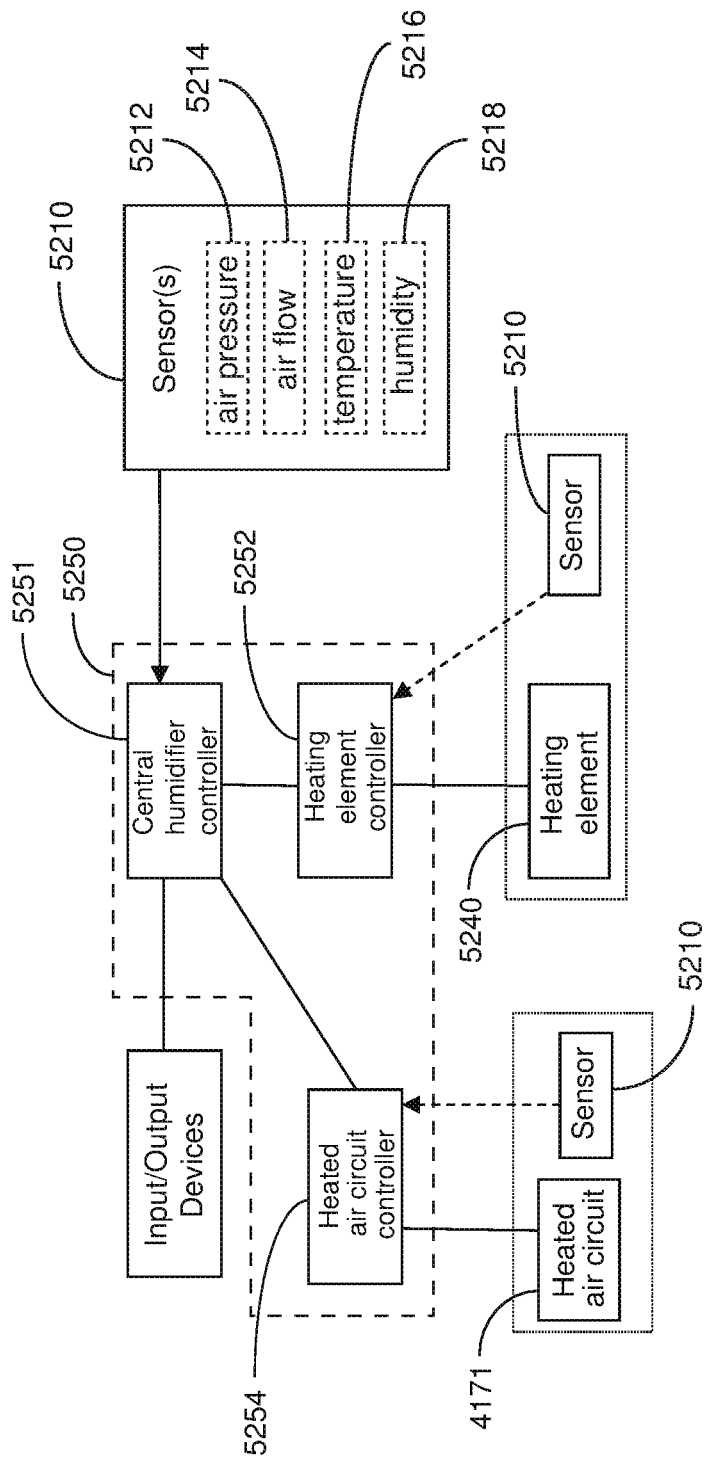

FIG. 21 shows a schematic of a humidifier in accordance with one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 TREATMENT SYSTEMS

Figure 1A:
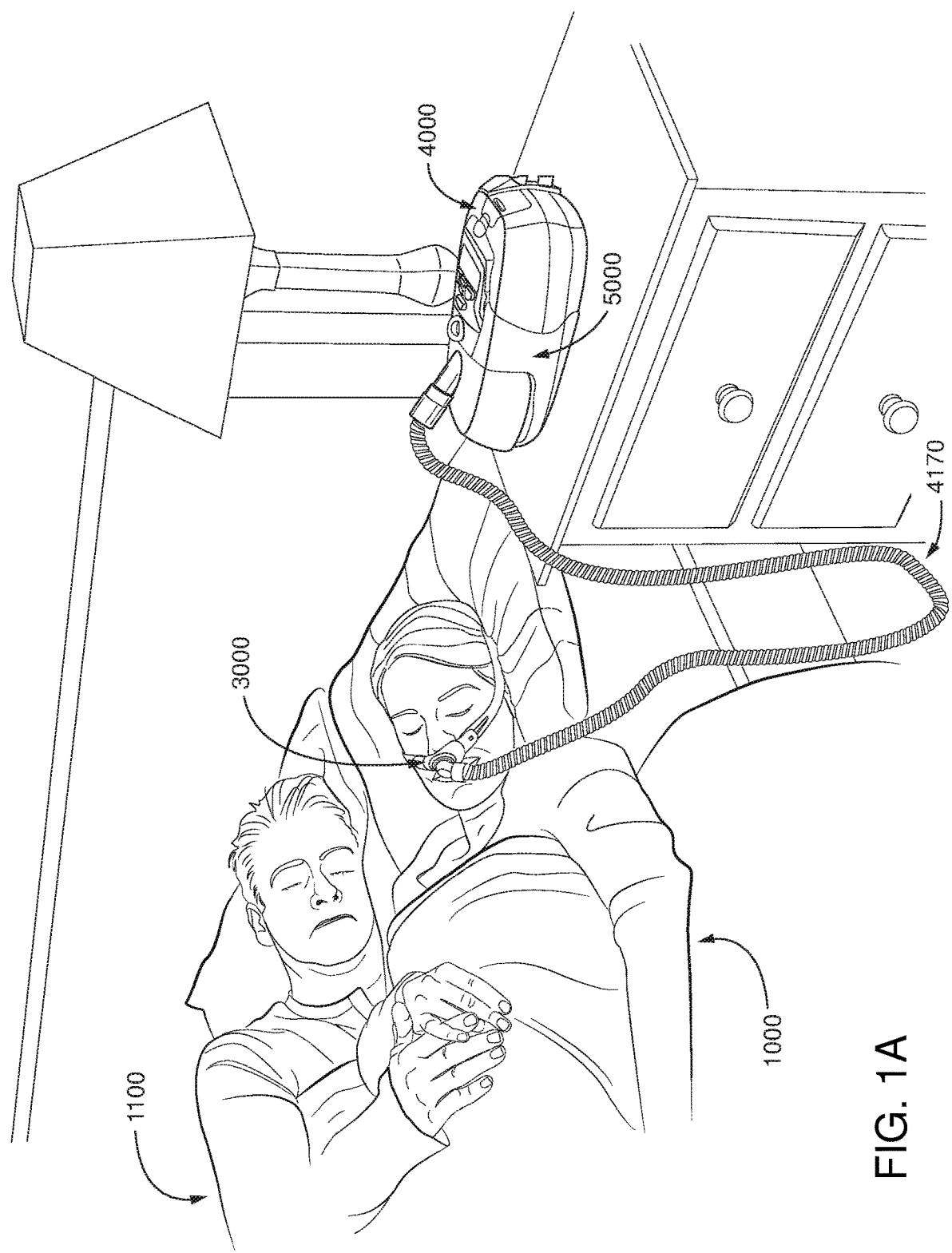
Figure 1B:
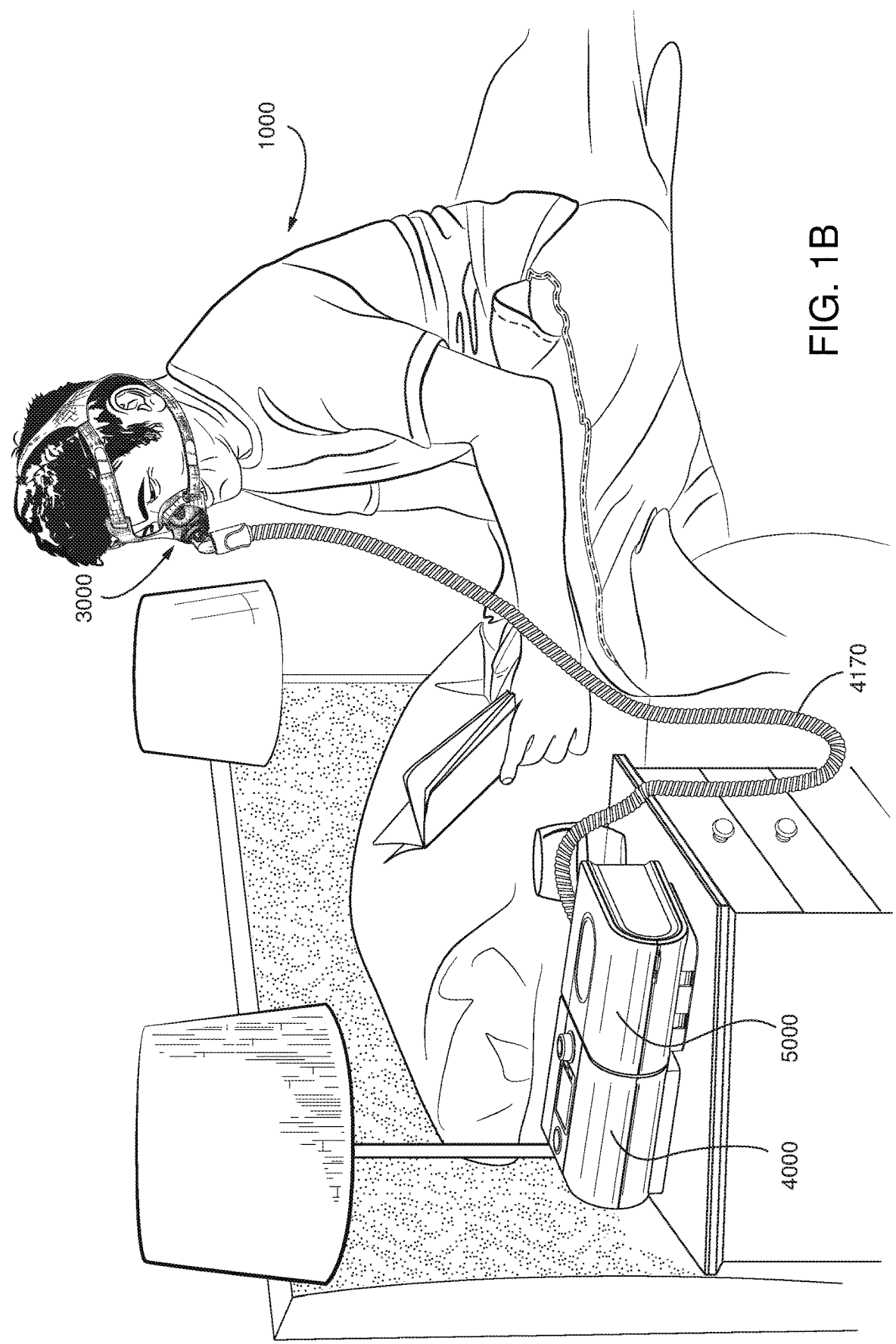
Figure 1C:
Figure 2A:
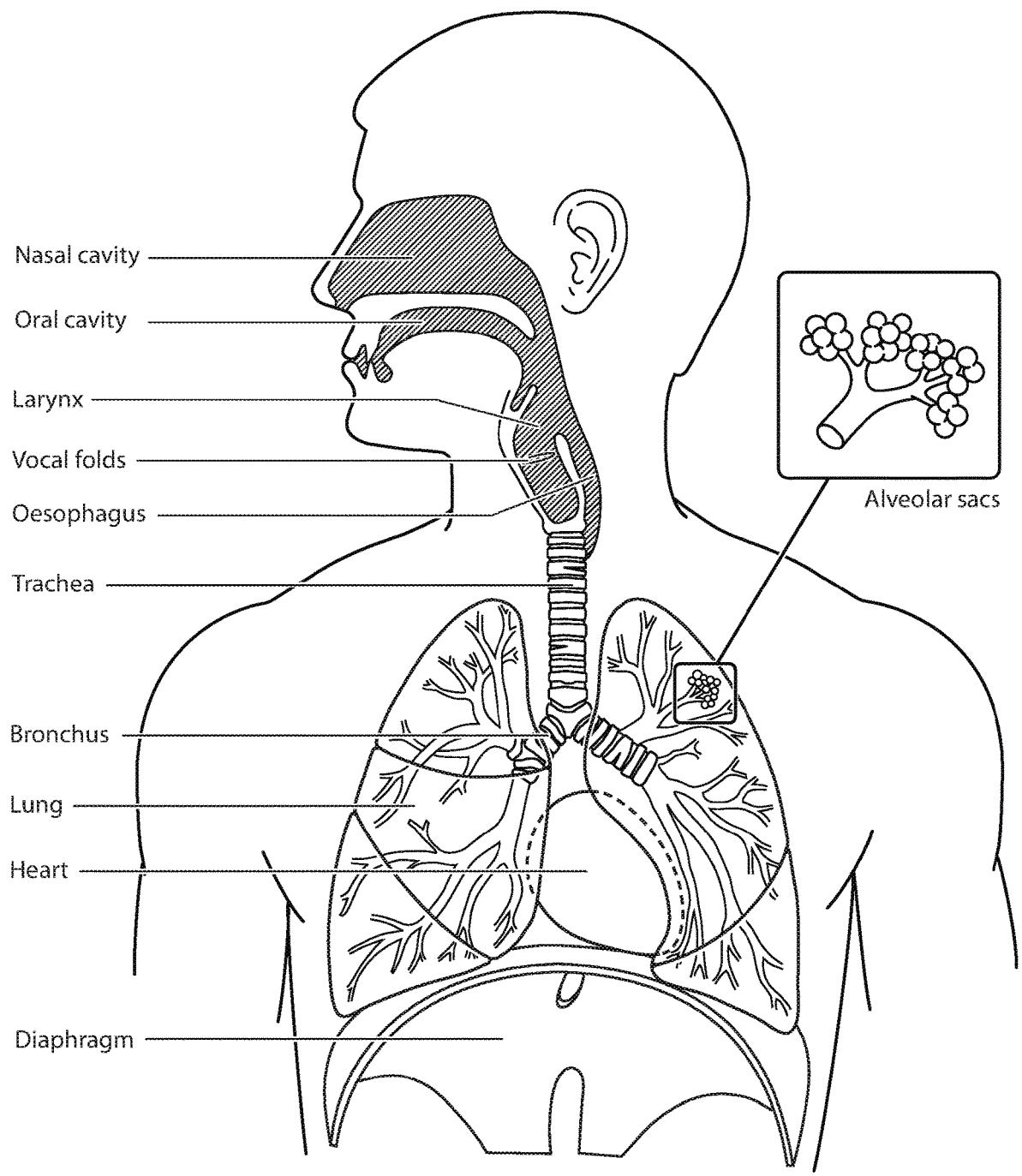
FIG. 2A shows an overview of a human respiratory system including the nasal and oral cavities, the larynx, vocal folds, oesophagus, trachea, bronchus, lung, alveolar sacs, heart and diaphragm.
Figure 2B:
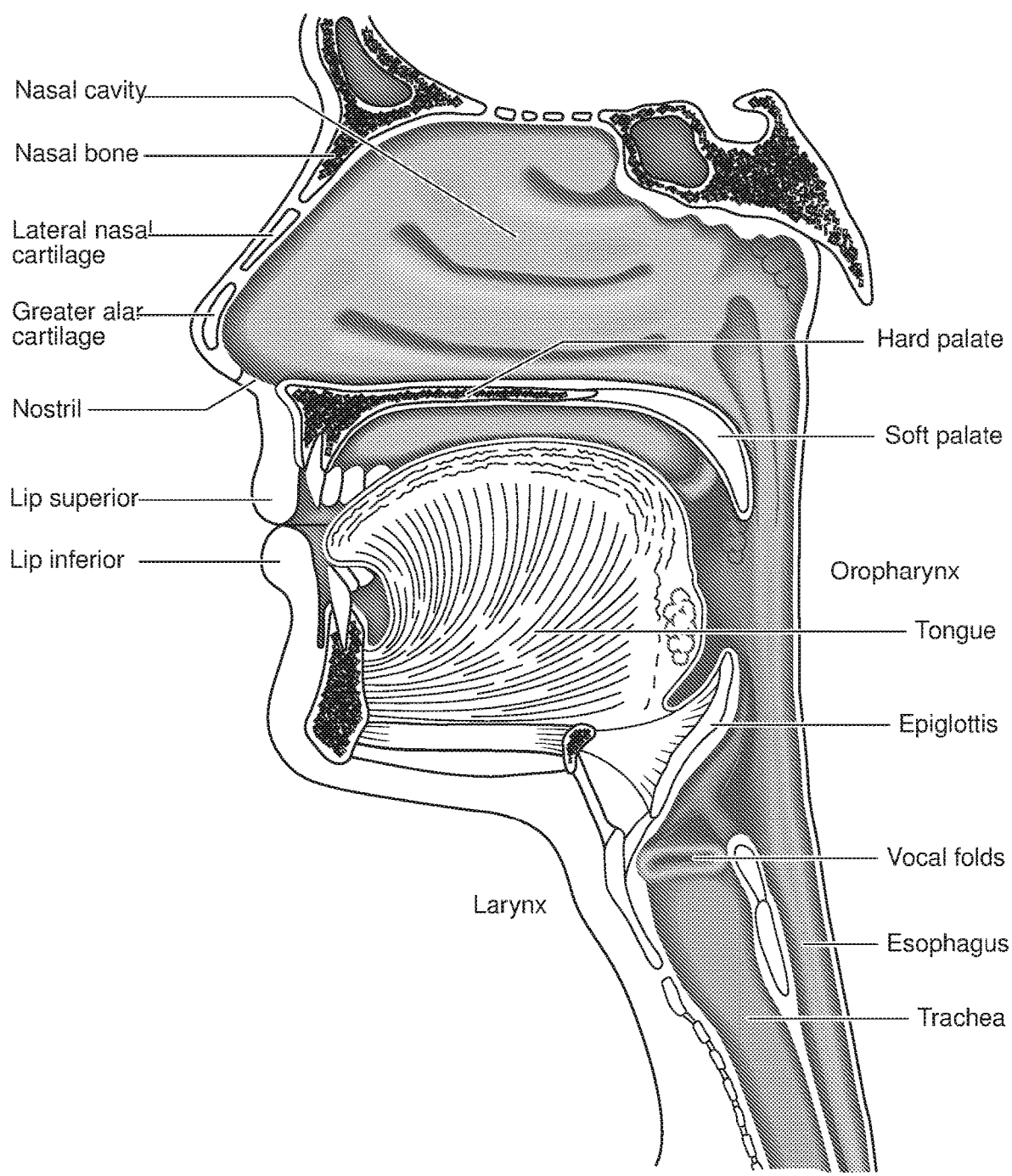
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 PATIENT INTERFACE

As shown in FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT DEVICE

An RPT device 4000 in accordance with one aspect of the present technology comprises mechanical, pneumatic, and/ or electrical components and is configured to execute one or more algorithms, e.g., see FIG. 4A. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

A power supply may be located internal or external of the external housing of the RPT device 4000.

In one form of the present technology, power supply provides electrical power to the RPT device only. In another form of the present technology, power supply provides electrical power to both RPT device 4000 and humidifier 5000.

In one form of the present technology, the RPT device 4000 includes a central controller including one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers, one or more input devices, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.6 HUMIDIFIER

5.6.1 Humidifier Overview

In one form of the present technology there is provided a humidifier to change the absolute humidity of air or gas for delivery to a patient relative to ambient air. Typically, the humidifier is used to increase the absolute humidity and increase the temperature of the flow of air (relative to ambient air) before delivery to the patient's airways.

FIGS. 5 to 8 show a RPT device 4000 and an integrated humidifier 5000 according to an example of the present technology. In the illustrated example, the humidifier 5000 includes a water reservoir dock 5130 structured to receive a water reservoir 5110. As shown, the water reservoir dock 5130 includes a cavity 5160 formed therein to receive the water reservoir 5110, e.g., the water reservoir 5110 may be insertable/removable from the water reservoir dock 5110 in a lateral direction.

In the illustrated example, the RPT device 4000 is integrated with the humidifier 5000. As this arrangement, the water reservoir dock 5130 is structured to connect the water reservoir 5110 to the pneumatic path. As best shown in FIGS. 5 and 8, the reservoir dock 5130 comprises a dock air outlet 5168 to deliver a flow of air to the water reservoir 5110, a dock air inlet 5170 to receive the flow of air that has been humidified in the water reservoir 5110, and a humidifier outlet 5172 to transfer the flow of humidified air to the air circuit 4170. The cavity 5160 may include a top portion configured to cover at least a portion of the lid of the water reservoir 5110 and a bottom portion including a heater plate 5120.

However, it should be appreciated that the reservoir dock 5130 may be provided separately to RPT device 4000 in an alternative arrangement. In such an arrangement, additional interfaces may be used to connect the reservoir dock 5130 to the RPT device 4000, e.g., directly coupled or coupled via an air circuit.

In another arrangement, the water reservoir dock 5130 may comprise an opening in a substantially horizontal plane, so that the water reservoir 5110 may be inserted from above or below the water reservoir dock 5130.

Further examples and details of such RPT device 4000 and integrated humidifier 5000 are described in PCT Publication No. WO 2014/138804, published Sep. 18, 2014, which is incorporated herein by reference in its entirety.

5.6.2 Humidifier Components

5.6.2.1 Water Reservoir

FIGS. 9 to 12 show one form of a water reservoir or tub 5110, which comprises a reservoir base 5112, a reservoir lid 5114, and an intermediate portion including a compliant portion 5116. The water reservoir 5110 includes a cavity (e.g., provided by the base) configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

In the illustrated example, the reservoir lid 5114 comprises an inlet 5118 for receiving the flow of air into the reservoir 5110 and an outlet 5122 for delivering a flow of air from the reservoir 5110. The reservoir lid 5114 is pivotably connected to the base 5112 by hinges 5158 to allow the reservoir 5110 to be converted between a closed configuration, as shown in FIGS. 9 to 11, and an open configuration, as shown in FIG. 12. When the water reservoir 5110 is in its closed configuration, the compliant portion 5116 is put into sealing engagement between the base 5112 and the lid 5114 to seal the base 5112 and the lid 5114 and prevent egress of water from the reservoir 5110. The compliant portion 5116 may also perform other functions, such as to improve thermal contact between the reservoir 5110 and the heater plate 5120.

The reservoir base 5112 may be configured as a receptacle to retain the given, maximum volume of liquid that the reservoir 5110 is configured to hold. In one form, the base 5112 may comprise further features such as an overfill prevention feature, e.g., at least one orifice 5138 in the water reservoir 5110 to indicate over-filling as shown in FIG. 13

In one form, the reservoir base 5112 may further comprise an inner lip 5224 and/or an outer lip 5226, for example as shown in FIG. 13. According to one aspect, the inner lip 5224 and/or outer lip 5226 may prevent egress of liquid from the reservoir 5110 through the interface between an intermediate portion (e.g. the compliant portion 5116) and the base 5112, for example when the intermediate portion is compressed, or when the intermediate portion is under vibration.

In one form, the reservoir base 5112 includes a base upper body 5146, a base bottom plate 5148, and a conductive portion 5152 which together form a receptacle, e.g., see FIG. 15. However, it should be appreciated that the reservoir base 5112 may be constructed in any number of parts.

In an example, the base upper body 5146, the base bottom plate 5148 and/or the lid 5114 may be constructed from a bio-compatible material suitable for retaining the volume of liquid, such as a plastic or thermoplastic polymer, for example, acrylonitrile butadiene styrene (ABS) or polycarbonate material.

In an example, a sealing element may be provided, e.g., between the base upper body 5146 and the base bottom plate 5148, to prevent egress of water from the water reservoir 5110, particularly from the base 5112.

Further examples and details of such water reservoir are described in PCT Publication No. WO 2014/138804, published Sep. 18, 2014, which is incorporated herein by reference in its entirety.

5.6.2.2 Conductive Portion

According to an example of the present technology, the reservoir 5110 comprises a conductive portion 5152 configured to allow efficient transfer of heat from the heater plate 5120 to the volume of liquid in the reservoir 5110. The conductive portion 5152 comprises a heat conducting material structured and arranged for thermal engagement or contact with the heater plate 5120 so as to allow thermal transfer of heat from the heater plate to the volume of liquid.

In the illustrated example of FIGS. 13 to 20, the conductive portion 5152 comprises a thin film (also referred to as a film base or a base conductor film) comprising a thermally conductive, non-metallic material configured to thermally couple with the heater plate 5120 of the humidifier 5000.

In an example, the heat conducting, non-metallic material of the thin film 5152 may comprise silicone, polycarbonate, or other thermoplastic or elastomeric materials.

In an example, the thin film 5152 may comprise a thickness of about 0.05 mm to 1.5 mm, e.g., 0.10 mm to 0.125 mm. In an example, the thin film may comprise a thickness less than about 1 mm, e.g., less than about 0.5 mm. In one form the film may comprise a silicone (LSR) film having a thickness of about 0.4 mm.

In the illustrated example, the base bottom plate 5148 includes side walls 5149.1 extending around the perimeter of the base bottom plate and a bottom wall 5149.2 that joins the side walls 5149.1, e.g., see FIG. 17. The thin film 5152 is provided or otherwise incorporated into the bottom wall 5149.2 to form the receptacle for retaining liquid. In the illustrated example, the bottom wall 5149.2 includes a hole 5149.3 structured to receive the thin film 5152, e.g., see FIG. 15. The thin film 5152 is sealingly secured within and/or across the hole 5149.3 in an operative position so as to form at least a portion of the base of the receptacle and prevent egress of water from the water reservoir 5110.

For example, the thin film 5152 may include a shape that corresponds to the shape of the hole 5149.3 such that the interior surface bounding the hole 5149.3 is secured against edges at the perimeter of the thin film 5152. Alternatively, the thin film 5152 may include a shape that is different than the shape of the hole 5149.3 such that the edges at the perimeter of the thin film 5152 extend beyond edges of the hole 5149.3, e.g., thin film 5152 overlaps bottom wall 5149.2 of the base bottom plate 5148. In the illustrated example, the thin film 5152 includes a shape that generally corresponds to a shape of the heater plate 5120, e.g., rectangular, however other suitable shapes are possible, e.g., square, circular, oval.

As illustrated, the thin film 5152 includes a first side 5152.1 adapted to form a bottom interior surface of the reservoir 5110 exposed to the water. The thin film 5152 includes a second side 5152.2, opposite to the first side 5152.1, adapted to form a bottom exterior surface of the reservoir 5110 exposed to the heater plate 5120, e.g., second side 5152.2 of the thin film 5152 provides a contact surface structured and arranged to directly engage with the heater plate 5120.

In the illustrated example, the thin film 5152 is generally planar and provided at the bottom of the reservoir. However, the thin film 5152 may comprise a non-planar shape and may be provided in other regions of the reservoir, e.g., provided along a side wall of the reservoir exposed to the water. In an example, the thin film 5152 may overlap one or more walls of the base bottom plate 5148, e.g., thin film extends across hole in the base bottom plate and shaped to conform and overlap with bottom and/or side walls of the base bottom plate 5148.

In an example, the film 5152 is provided as a separate and distinct structure from the base bottom plate 5148 and then secured or otherwise provided to the base bottom plate 5148 in an operative position, e.g., film 5152 comprises a pre-formed structure that is secured to the base bottom plate 5148.

In an example, the film 5152 may be pre-formed, and then insert moulded to the base bottom plate 5148. In another example, the film 5152 may be pre-formed and then secured to the base bottom plate 5148, e.g., by adhesives or welding. In yet another example, the film 5152 may be provided to the base bottom plate 5148 by overmoulding the film 5152 to the base bottom plate 5148.

In an example, the base bottom plate 5148 may be eliminated, or the film may be supported or reinforced in other ways, e.g., at least one reinforcing strip of a more rigid material compared to the film, embedded into or otherwise provided to the film. In an example, the film may be provided to the base upper body 5146 such that the film constitutes the entire bottom of the reservoir.

In arrangements where a pre-formed film 5152 is provided to the base bottom plate 5148 (e.g., insert-moulded or adhered), the film may comprise a thermoplastic polycarbonate film material (e.g., Makrofol DE 1-4 material of about 0.1 mm thickness), and the base bottom plate 5148 may comprise a thermoplastic polycarbonate material (e.g., Makrolon 2458 (or Makrolon 2258) material). However, it should be appreciated that the pre-formed film and/or the base bottom plate may comprise other suitable materials.

In an example, the film may be filled with one or more additives to promote thermal conductivity, in which case the film may be thicker, e.g., for added mechanical stability.

For example, the film may comprise ceramic powder or metallic powder filled plastics, or the film may comprise multiple films or layers, e.g., sandwich laminates including a metallic film with a plastic film on one or both sides of the metallic film.

In an example, powder-coating or spray painting with thermally conductive materials (e.g., metals) may be applied to the second side 5152.2 of the film facing the heater plate 5120 to improve thermal conductivity.

In an example, the film 5152 may comprise a thickness that is different than a thickness of the bottom and/or side walls of the base bottom plate 5148, e.g., wall thickness of the film is less than the wall thickness of the bottom and/or side walls of the base bottom plate 5148. Such arrangement allows the thickness of the film to be suitably selected to achieve desired performance characteristics, e.g., performance at high flows, humidification rate, heat-up time.

In an example, the film 5152 may comprise a material similar to the material of the base upper body 5146 and/or the base bottom plate, with the film 5152 comprising a wall thickness that is less than a wall thickness of walls of the base upper body 5146 and/or the base bottom plate 5148.

In an example, as shown in FIGS. 18 to 20, the reservoir 5110 may be provided with one or more ribs 5175 structured and arranged to extend across the thin film 5152 so as to create a force adapted to push the thin film 5152 against the heater plate 5120.

Alternatively or in addition, the humidifier may be provided with a spring-like element structured and arranged to push the heater plate 5120 against the thin film 5152.

The thin film base 5152 of the reservoir provides an arrangement that reduces cost of production of the reservoir, while retaining, or improving, its heat transfer characteristics as well as its reliability. For example, the thin film base is advantageous in that the thin film base may be sufficiently thin and flat to provide good thermal contact and good humidifier performance and allow a suitable material to be selected, e.g., depending on humidifier requirements and performance.

In an example, the thin film base may be advantageous in that the non-metallic properties of the thin film base (e.g., thermoplastic or elastomeric material properties) provides corrosion protection (e.g., protection due to exposure to water) and a sealed connection with the base bottom plate 5148 (e.g., to form a sealed reservoir for the humidification water). Also, the non-metallic properties of the thin film base (e.g., thermoplastic or elastomeric material properties) may facilitate manufacture of the thin film base to assume complex shapes, e.g., thin film base may be molded into complex shapes if required to meet design requirements of the humidifier. Further, the reduced cost of production of the reservoir is particularly desirable in the case of a disposable reservoir in which the reservoir is intended only for a limited product life where a hospital, a patient or a user replaces the reservoir on a regular basis.

5.6.2.3 Humidifier Reservoir Dock

As described above, the humidifier 5000 may comprise a humidifier reservoir dock 5130 (as shown in FIGS. 5 to 8) configured to receive the humidifier reservoir 5110. In some arrangements, the humidifier reservoir dock 5130 may comprise a locking feature configured to retain the reservoir 5110 in the humidifier reservoir dock 5130.

5.6.2.4 Water Level Indicator

The humidifier reservoir 5110 may comprise a water level indicator. In some forms, the water level indicator may provide one or more indications to a user such as the patient 1000 or a care giver regarding a quantity of the volume of water in the humidifier reservoir 5110. The one or more indications provided by the water level indicator may include an indication of a maximum, predetermined volume of water, any portions thereof, such as 25%, 50% or 75% or volumes such as 200 ml, 300 ml or 400 ml.

5.6.2.5 Humidifier Transducer(s)

As shown in FIG. 21, the humidifier 5000 may comprise one or more humidifier transducers (sensors) 5210 instead of, or in addition to, transducers provided in the RPT device 4000. Humidifier transducers 5210 may include one or more of an air pressure sensor 5212, an air flow rate transducer 5214, a temperature sensor 5216, or a humidity sensor 5218 as shown in FIG. 21. A humidifier transducer 5210 may produce one or more output signals which may be communicated to a controller such as a central controller of the RPT device 4000 and/or a central humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor provided in the RPT device 4000.

5.6.2.5.2 Flow Rate Transducer

One or more flow rate transducers 5214 may be provided to the humidifier 5000 in addition to, or instead of, a flow rate sensor provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base where heat may be provided to the humidifier reservoir 5110 primarily by conduction.

5.6.2.7 Humidifier Controller

According to one arrangement of the present technology, a humidifier 5000 may comprise a humidifier controller 5250 as shown in FIG. 21. In one form, the humidifier controller 5250 may be a part of the central controller of the RPT device 4000. In another form, the humidifier controller 5250 may be a separate controller, which may be in communication with the central controller.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 21, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 GLOSSARY

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.3 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.3.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.3.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.3.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.7.3.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 REFERENCE SIGNS LIST

Feature Item Number
patient 1000
bed partner 1100
patient interface 3000
seal-forming structure 3100
plenum chamber 3200
stabilizing structure 3300
vent 3400
connection port 3600
forehead support 3700
RPT device 4000
air circuit 4170
humidifier 5000
water reservoir 5110
reservoir base 5112
reservoir lid 5114
compliant portion 5116
inlet 5118
heater plate 5120
outlet 5122
water reservoir dock 5130
orifice 5138
base upper body 5146
base bottom plate 5148
side wall 5149.1
bottom wall 5149.2
hole 5149.3
thin film 5152
first side 5152.1
second side 5152.2
hinge 5158
cavity 5160
dock air outlet 5168
dock air inlet 5170
humidifier outlet 5172
rib 5175
humidifier transducer 5210
air pressure sensor 5212
air flow rate transducer 5214
temperature sensor 5216
humidity sensor 5218
inner lip 5224
outer lip 5226
heating element 5240
humidifier controller 5250
central humidifier controller 5251
heating element controller 5252
air circuit controller 5254

The invention claimed is:

1. A water reservoir for an apparatus for humidifying a flow of breathable gas, the water reservoir constructed and arranged to removably engage with a heater plate of the apparatus when in an operative position to provide heat to a volume of liquid in the water reservoir, the water reservoir comprising:
    a reservoir base including a cavity structured to hold the volume of liquid; and
    a thin film provided to the reservoir base,
    wherein the thin film comprises a direct, non-removable and sealed connection with the reservoir base so as to form at least a portion of the reservoir base for holding the volume of liquid,
    wherein the thin film is adapted to removably and thermally engage with the heater plate when the water reservoir is in the operative position to allow thermal transfer of heat from the heater plate to the volume of liquid in use,
    wherein the thin film includes a first side adapted to form a bottom interior surface of the water reservoir exposed to the volume of liquid and a second side, opposite to the first side,
    wherein the second side of the thin film is adapted to form a bottom, exposed exterior surface of the water reservoir exposable to the heater plate to allow removable and thermal engagement with the heater plate when the water reservoir is in the operative position,
    wherein the thin film comprises a non-metallic material, and
    wherein the thin film includes a wall thickness less than 1 mm, and
    further comprising one or more ribs structured and arranged to extend across the thin film so as to create a force adapted to push the thin film against the heater plate when the water reservoir is in the operative position.

2. The water reservoir according to claim 1, wherein the wall thickness is less than 0.5 mm.

3. The water reservoir according to claim 1, wherein the thin film comprises silicone, polycarbonate, or other thermoplastic or elastomeric materials.

4. The water reservoir according to claim 1, wherein the thin film is provided as a separate and distinct structure from the reservoir base.

5. The water reservoir according to claim 1, wherein the thin film comprises a pre-formed structure that is non-removably secured to the reservoir base.

6. The water reservoir according to claim 1, wherein the reservoir base includes a hole structured to receive the thin film.

7. The water reservoir according to claim 6, wherein the thin film includes a shape that corresponds to a shape of the hole.

8. The water reservoir according to claim 1, wherein the thin film is generally planar.

9. The water reservoir according to claim 1, wherein the second side of the thin film provides a contact surface structured and arranged to directly and removably engage with the heater plate when the water reservoir is in the operative position.

10. The water reservoir according to claim 1, wherein the non-metallic material of the thin film is similar to a material of the reservoir base.

11. The water reservoir according to claim 1, wherein the wall thickness of the thin film is less than a wall thickness of walls of the reservoir base.

12. The water reservoir according to claim 1, wherein the reservoir base includes a base upper body and a base bottom plate, and wherein the base upper body, the base bottom plate, and the thin film together form the cavity.

13. The water reservoir according to claim 1, further comprising a reservoir lid movably connected to the reservoir base to allow the water reservoir to be convertible between an open configuration and a closed configuration.

14. The water reservoir according to claim 1, wherein the water reservoir comprises a separate, insertable unit adapted for repeated, removable engagement with the heater plate of the apparatus.

15. The water reservoir according to claim 1, further comprising a reservoir lid, the reservoir lid comprising an inlet for receiving the flow of breathable gas into the water reservoir and an outlet for delivering a flow of humidified breathable gas from the water reservoir.

16. The water reservoir according to claim 1, wherein the thin film is structured and arranged to overlap with bottom and/or side walls of the reservoir base.

17. The water reservoir according to claim 1, wherein the thin film comprises an insert molded connection with the reservoir base.

18. The water reservoir according to claim 1, wherein the thin film comprises surfaces structured and arranged to directly contact with surfaces of the reservoir base to form said direct, non-removable and sealed connection with the reservoir base.

19. The water reservoir according to claim 18, wherein the reservoir base includes a bottom wall and side walls extending around a perimeter of the bottom wall, the bottom wall including a hole, and wherein the thin film is directly and sealingly connected to at least the bottom wall so that the thin film extends across the hole in said direct, non-removable and sealed connection with the reservoir base.

20. The water reservoir according to claim 19, wherein the thin film is further directly and sealingly connected to the side walls such that the thin film directly contacts and overlaps with the bottom wall and the side walls in said direct, non-removable and sealed connection with the reservoir base.

21. The water reservoir according to claim 19, wherein the thin film comprises a pre-formed structure that is directly and non-removably secured to at least the bottom wall in said direct, non-removable and sealed connection with the reservoir base.

22. A water reservoir for an apparatus for humidifying a flow of breathable gas, the water reservoir constructed and arranged to removably engage with a heater plate of the apparatus when in an operative position to provide heat to a volume of liquid in the water reservoir, the water reservoir comprising:

a reservoir base including bottom and side walls forming a cavity structured to hold the volume of liquid; and
a conductive portion provided to the reservoir base,
wherein the conductive portion comprises a direct, non-removable and sealed connection with the reservoir base so as to form at least a portion of the reservoir base for holding the volume of liquid,
wherein the conductive portion is adapted to removably and thermally engage with the heater plate when the water reservoir is in the operative position to allow thermal transfer of heat from the heater plate to the volume of liquid in use,
wherein the conductive portion includes a thin film comprising a non-metallic material,
wherein the thin film is provided as a separate and distinct structure from the reservoir base,
wherein the thin film includes a wall thickness that is less than a wall thickness of the bottom and side walls of the reservoir base,
wherein the thin film includes a first side adapted to form a bottom interior surface of the water reservoir exposed to the volume of liquid and a second side, opposite to the first side,
wherein the second side of the thin film is adapted to form a bottom, exposed exterior surface of the water reservoir exposable to the heater plate to allow removable and thermal engagement with the heater plate when the water reservoir is in the operative position, and
further comprising one or more ribs structured and arranged to extend across the thin film so as to create a force adapted to push the thin film against the heater plate when the water reservoir is in the operative position.

23. The water reservoir according to claim 22, wherein the thin film comprises a pre-formed structure that is non-removably secured to the reservoir base.

24. An apparatus for humidifying a flow of breathable gas, comprising:

a water reservoir including a cavity structured to hold a volume of liquid, the water reservoir comprising a reservoir base and a thin film provided to the reservoir base,
wherein the thin film comprises a direct, non-removable and sealed connection with the reservoir base so as to form at least a portion of the water reservoir for holding the volume of liquid,
wherein the thin film includes a first side adapted to form a bottom interior surface of the water reservoir exposed to the volume of liquid and a second side, opposite to the first side, adapted to form a bottom exterior surface of the water reservoir, wherein the thin film comprises a non-metallic material, and wherein the thin film includes a wall thickness less than 1 mm; and a water reservoir dock forming a cavity structured and arranged to removably receive the water reservoir in an operative position, the water reservoir dock including a heater plate adapted to removably and thermally engage the thin film of the water reservoir in the operative position to allow thermal transfer of heat from the heater plate to the volume of liquid in use, and further comprising one or more ribs structured and arranged to extend across the thin film so as to create a force adapted to push the thin film against the heater plate when the water reservoir is in the operative position.

25. The apparatus according to claim 24, wherein the water reservoir dock includes a dock air outlet to deliver the flow of breathable gas to the water reservoir.

26. The apparatus according to claim 24, wherein the water reservoir further comprises a reservoir lid, the reservoir lid comprising an inlet for receiving the flow of breathable gas into the water reservoir and an outlet for delivering a flow of humidified breathable gas from the water reservoir.

27. The apparatus according to claim 24, wherein the water reservoir is insertable to and removable from the water reservoir dock in a lateral direction.

* * * * *